US012565506B2

(12) United States Patent
Donnelly et al.

(10) Patent No.: US 12,565,506 B2
(45) **Date of Patent: *Mar. 3, 2026**

(54) NITROGEN-CONTAINING MACROCYCLIC CONJUGATES AS RADIOPHARMACEUTICALS

(71) Applicant: Clarity Pharmaceuticals Ltd., Eveleigh (AU)

(72) Inventors: Paul Stephen Donnelly, Victoria (AU); Michelle Therese Ma, Victoria (AU); Denis Bernard Scanlon, Meadows (AU)

(73) Assignee: CLARITY PHARMACEUTICALS LTD, Eveleigh (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/498,744

(22) Filed: Oct. 31, 2023

(65) Prior Publication Data

US 2024/0190897 A1 Jun. 13, 2024

Related U.S. Application Data

(60) Division of application No. 17/393,837, filed on Aug. 4, 2021, now Pat. No. 11,905,301, which is a continuation of application No. 16/712,485, filed on Dec. 12, 2019, now Pat. No. 11,111,254, which is a continuation of application No. 15/612,009, filed on Jun. 2, 2017, now Pat. No. 10,544,164, which is a continuation of application No. 13/132,194, filed as application No. PCT/AU2009/001572 on Dec. 2, 2009, now Pat. No. 9,701,694.

(30) Foreign Application Priority Data

Dec. 2, 2008 (AU) ................................ 2008906239

(51) Int. Cl.

| | |
|---|---|
| ***C07D 521/00*** | (2006.01) |
| ***A61K 51/04*** | (2006.01) |
| ***A61K 51/08*** | (2006.01) |
| *A61K 49/06* | (2006.01) |
| *A61K 49/08* | (2006.01) |
| *A61K 49/10* | (2006.01) |
| *A61K 51/00* | (2006.01) |
| *A61K 51/02* | (2006.01) |
| *A61K 51/10* | (2006.01) |

(52) U.S. Cl.

CPC ........ *C07D 521/00* (2013.01); *A61K 51/0482* (2013.01); *A61K 51/082* (2013.01); *A61K 51/088* (2013.01); *A61K 49/06* (2013.01); *A61K 49/08* (2013.01); *A61K 49/10* (2013.01); *A61K 49/101* (2013.01); *A61K 51/00* (2013.01); *A61K 51/02* (2013.01); *A61K 51/04* (2013.01); *A61K 51/08* (2013.01); *A61K 51/10* (2013.01); *A61K 51/106* (2013.01)

(58) Field of Classification Search

CPC ...... C07D 521/00; A61K 51/04; A61K 49/10; A61K 49/08; A61K 49/101; A61K 49/06; A61K 51/00; A61K 51/02

See application file for complete search history.

(56) References Cited

U.S. PATENT DOCUMENTS

| | | | | |
|---|---|---|---|---|
| 5,245,055 | A * | 9/1993 | Kronenthal .......... | C07D 493/08 549/463 |
| 6,107,326 | A | 8/2000 | Jori | |
| 6,869,589 | B1 | 3/2005 | Smith et al. | |
| 2010/0040542 | A1 | 2/2010 | Archer et al. | |
| 2010/0260676 | A1 | 10/2010 | Hanson et al. | |

FOREIGN PATENT DOCUMENTS

| | | | |
|---|---|---|---|
| JP | H04-244085 | A | 9/1999 |
| JP | 2005-500325 | A | 1/2005 |
| WO | 9531202 | | 11/1995 |
| WO | 03/006070 | A2 | 1/2003 |
| WO | 03063912 | | 8/2003 |
| WO | 2005037862 | | 4/2005 |

OTHER PUBLICATIONS

Bales et al., "Mechanistic studies on DNA damage by minor groove binding copper-phenanthroline conjugates", Nucleic Acids Research, 2005, vol. 33, No. 16, 5371-5379.

Sykes, "A Guide to Mechanism in Organic Chemistry." Sixth Edition (1986), pp. 200-201.

Paterson et al., "PET imaging of tumours with a 64Cu labeled macrobicyclic cage amine ligand tethered to Tyr3-Jctreotate", Dalton Trans. 2014, vol. 43, pp. 1386-1396.

Geue et al., "A New Template Encapsulation Strategy for Larger Cavity Metal Ion Cages", Journal of the Chemical Society, Chemical Communications, pp. 1513-1515.

International Search Report of PCT/AU2009/001572 mail dated Mar. 10, 2010 (3 pages).

Written Opinion of PCT/AU2009/001572 dated Feb. 12, 2010 (7 pages).

(Continued)

*Primary Examiner* — James W Rogers

(74) *Attorney, Agent, or Firm* — McBee Moore & Vanik IP, LLC

(57) ABSTRACT

The present invention relates to compounds that are useful as metal ligands and which either contain a molecular recognition moiety or can be bound to a molecular recognition moiety and methods of making these compounds. Once the compounds that contain a molecular recognition moiety are coordinated with a suitable metallic radionuclide, the coordinated compounds are useful as radiopharmaceuticals in the areas of radiotherapy and diagnostic imaging. The invention therefore also relates to methods of diagnosis and therapy utilising the radiolabelled compounds of the invention.

6 Claims, No Drawings

Specification includes a Sequence Listing.

(56) References Cited

OTHER PUBLICATIONS

Kramer, Andreas et al., Derivatives of 1,3,5-Tramino-1,3,5-trideoxy-cis-inosotol as Versatile Pentadentate Ligands 7 or Protein Labeling with Re-186/188. Prelabeling, Biodistribution, and X-ray Structural Studies. Bioconjugage Chem 19989, 691-702.
Lengkeek, Nigel B. Sc. {Hons) B.E. {Hons), "Functional Cage-Amine Complexes: Polymerisable Metallomonomers and Multi-Cage Complexes".

* cited by examiner

NITROGEN-CONTAINING MACROCYCLIC CONJUGATES AS RADIOPHARMACEUTICALS

CROSS REFERENCE TO RELATED APPLICATIONS

This application is a Divisional application of U.S. application Ser. No. 17/393,837, filed Aug. 4, 2021, which is a Continuation application of U.S. application Ser. No. 16/712,485, filed Dec. 12, 2019, now U.S. Pat. No. 11,111,254, issued Sep. 7, 2021, which is a continuation of U.S. application Ser. No. 15/612,009, filed Jun. 2, 2017, now U.S. Pat. No. 10,544,164, issued Jan. 28, 2020, which is a Continuation application of U.S. application Ser. No. 13/132,194, filed on Aug. 22, 2011, now U.S. Pat. No. 9,701,694, issued on Jul. 11, 2017, which is a National Stage Application of PCT/AU2009/001572, filed Dec. 2, 2009, which claims priority to Australian Application 2008906239, filed Dec. 2, 2008, the contents of which are incorporated by reference herein in their entireties.

REFERENCE TO SEQUENCE LISTING XML

Pursuant to the EFS-Web legal framework and 37 CFR §§ 1.821-825 (see MPEP § 2442.03(a)), a Sequence Listing in extensible Markup Language (XML) format (entitled "Sequence_listing_2913474-009006_ST26.xml" created on Oct. 31, 2023, and 4,758 bytes in size) is submitted concurrently with the instant application, and the entire contents of the Sequence Listing are incorporated herein by reference.

FIELD

The present invention relates to compounds that are useful as metal ligands and which either contain a molecular recognition moiety or can be bound to a molecular recognition moiety and methods of making these compounds. Once the compounds that contain a molecular recognition moiety are coordinated with a suitable metallic radionuclide, the coordinated compounds are useful as radiopharmaceuticals in the areas of radiotherapy and diagnostic imaging. The invention therefore also relates to methods of diagnosis and therapy utilising the radiolabelled compounds of the invention.

BACKGROUND

Radiolabelled compounds may be used as radiopharmaceuticals in a number of applications such as in radiotherapy or diagnostic imaging. In order for a radiolabelled compound to be employed as a radiopharmaceutical there are a number of desirable properties that the compound should ideally possess such as acceptable stability and, where possible, a degree of selectivity or targeting ability.

Initial work in the areas of radiopharmaceuticals focused on simple metal ligands which were generally readily accessible and hence easy to produce. A difficulty with many of these radiolabelled compounds is that the complex formed between the ligand and the metal ion was not sufficiently strong and so dissociation of the metal ion from the ligand occurred in the physiological environment. This was undesirable as with the use of ligands of this type there was no ability to deliver the radiopharmaceutical to the desired target area in the body as metal exchange with metal ions in the physiological environment meant that when the radiopharmaceutical compound arrived at the desired site of action the level of radiolabelled metal ion coordinated to the compound had become significantly reduced. In addition where this type of exchange is observed the side effects experienced by the subject of the radiotherapy or radioimaging are increased as radioactive material is delivered to otherwise healthy tissue in the body rather than predominantly to its place of action.

In order to overcome the problem of metal dissociation in the physiological environment a number of more complicated ligands have been developed and studied over time. Thus, for example a wide range of tetra-azamacrocycles based on the cyclam and cyclen framework have been investigated. Examples of ligands of this type include DOTA and TETA.

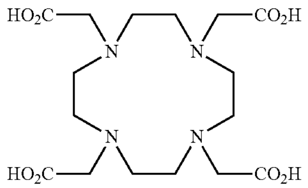

DOTA

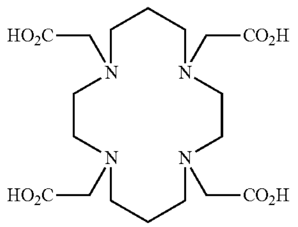

TETA

Unfortunately, even with these ligands there is still dissociation of the metal with certain derivatives. For example, some derivatives suffer from dissociation of Cu from the chelate as a consequence of transchelation to biological ligands such as copper transport proteins either as $Cu^{2+}$ or following in vivo reduction to Cut.

In order to increase the stability of radiolabelled compounds therefore hexaminemacrobicyclic cage amine ligands, known by their trivial name sarcophagines have been developed. These cage ligands form remarkably stable complexes with metals such as $Cu^{2+}$ and have fast complexation kinetics even at low concentrations of metal at ambient temperatures. These features therefore make ligands of this type particularly well suited in radiopharmaceutical applications, especially those applications involving copper.

Once the problem of stability of the complex between the ligand and the metal had been overcome attention turned to developing ways in which the ligand could be functionalised to incorporate targeting molecules within the ligand without compromising the stability of the metal ligand complex or the ultimate biological activity of the targeting molecule. A number of different targeting molecules are known in the art and the issue became how best to attach these to the ligand molecules.

In general the targeting molecule (or molecular recognition moiety as it is sometimes known) is attached to the ligand to provide a final compound containing both a ligand and a molecular recognition moiety. Whilst these compounds may contain a single molecular recognition moiety they may also be multimeric constructs where the ligand is attached to two (or more) molecular recognition moieties. This is typically desirable as a multimeric construct can possess higher affinity for a target receptor than its monomeric equivalent. This is in part due to an increase in the local concentration of the targeting group, allowing it to compete more effectively with endogenous ligands. In addition in circumstances where there is sufficient length between two or more targeting groups within a multimeric construct, then cooperative binding is possible, and two or more targeting groups will bind to two or more receptor sites at the same time. Indeed it has been observed that in vivo, a multimeric construct often demonstrates higher target tissue accumulation than its monomeric equivalent.

Without wishing to be bound by theory it is thought that this is due to the higher affinity of the multimeric construct for the target receptor than that of the monomeric construct. Furthermore, the multimeric construct has a higher molecular weight than the monomeric construct and therefore prolonged bioavailability (as it is more resistant to degradation in the physiological environment). This can result in increased accumulation and retention in target tissue.

Initial work in the caged ligand area looked at direct coupling reactions of the primary amines of the cage amine 'diaminosarcophagine', 1,8-diamino-3,6,10,13,16,19-hexaaza bicyclo[6.6.6] icosane ($(NH_2)_2$sar), with peptides using standard coupling procedures. Unfortunately for a variety of reasons this has proven to be relatively inefficient and work in this area ceased. Workers then focussed on the incorporation of an aromatic amine to produce SarAr. The pendent aromatic amine can be used in conjugation reactions with the carboxylate residues of peptides or antibodies and it has been shown that SarAr could be conjugated to anti-GD2 monoclonal antibody (14.G2a) and its chimeric derivative (ch14.8) and the conjugate has been radiolabelled with $^{64}$Cu.

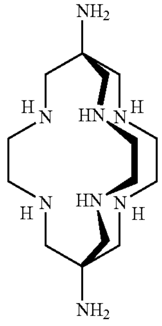

$(NH_2)_2$sar

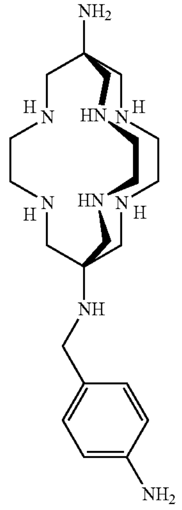

SarAr

A difficulty with this approach is that in reaction of the aromatic amine in the conjugation step there are 8 other nitrogen atoms in the SarAr molecule that are available for competing reactions leading to the potential for the creation of a large number of impurities that is undesirable from a pharmaceutical sense. Whilst these could potentially be overcome by the use of substantial protective group chemistry this is clearly undesirable from a synthetic standpoint and scale up on a commercial scale.

An alternative approach has been to elaborate the ligand to incorporate carboxylate functional groups and incorporate peptides or antibodies via their N-terminal amine residues and this approach is of particular importance when the C-terminus is crucial to biological activity. Studies have shown that $(NH_2)_2$sar, can be functionalised with up to four carboxymethyl substituents via alkylation reactions with chloroacetic acid and the introduced carboxymethyl arms can be used as a point of further functionalisation and EDC-coupling reactions can then be used to introduce amino acids.

Unfortunately a potential disadvantage of these systems is that intramolecular cyclisation reactions can still occur in which the carboxymethyl arm reacts with a secondary amine of the cage framework to form lactam rings resulting in quadridentate rather than sexidentate ligands. Accordingly whilst this approach can be followed the potential for unwanted side reactions is clearly undesirable from a commercial perspective.

Accordingly there is still a need to develop compounds that are capable of being radiolabelled and which contain, or are capable of being bound to a molecular recognition moiety that can be used in radiopharmaceutical applications. In addition it would be desirable if the compounds had the flexibility to provide for the possibility of multimeric constructs being used as in certain circumstances these constructs demonstrate higher biological activity as discussed above.

SUMMARY

In one aspect there is provided a compound of formula (I),

Formula (I)

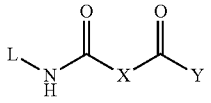

wherein:

L is a nitrogen containing macrocyclic metal ligand;

X is a linking moiety;

Y is selected from the group consisting of OR, $SR^1$ and $N(R^2)_2$;

R is independently selected from the group consisting of H, an oxygen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

$R^1$ is independently selected from the group consisting of H, a sulfur protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

each $R^2$ is independently selected from the group consisting of H, a nitrogen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

or a pharmaceutically acceptable salt or complex thereof.

In a further aspect there is provided a compound of formula (II),

Formula (II)

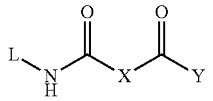

wherein:

L is a nitrogen containing macrocyclic metal ligand;

X is a linking moiety;

Y is a molecular recognition moiety;

or a pharmaceutically acceptable salt or complex thereof.

As with any group of structurally related compounds which possess a particular utility, certain embodiments of variables of the compounds of the formula (I) and formula (II), which are particularly useful in their end use application.

In the compounds of formula (I) and formula (II) the X moiety serves as a linking moiety that serves to act as a spacer between the two carbonyl moieties which separate the ligand which can be bound to the radionuclide and either the point of attachment of a molecular recognition moiety or the molecular recognition moiety per se. As such whilst it is desirable that there be a certain degree of separation between the two in order to ensure that the two entities do not interfere with each other's activity it is also important that the two are not so far removed such that the radionuclide is not effectively delivered to its site of operation.

In some embodiments X is a linking moiety having from 1 to 20 atoms in the normal chain. In some embodiments X is a linking moiety having from 1 to 15 atoms in the normal chain. In some embodiments X is a linking moiety having from 1 to 12 atoms in the normal chain. In some embodiments X is a linking moiety having from 1 to 10 atoms in the normal chain. In some embodiments X is a linking moiety having from 1 to 8 atoms in the normal chain. In some embodiments X has 8 atoms in the normal chain. In some embodiments X has 7 atoms in the normal chain. In some embodiments X has 6 atoms in the normal chain. In some embodiments X has 5 atoms in the normal chain. In some embodiments X has 4 atoms in the normal chain. In some embodiments X has 3 atoms in the normal chain. In some embodiments X has 2 atoms in the normal chain. In some embodiments X has 1 atom in the normal chain.

A wide range of possible moieties may be use to create a linking moiety of this type. Examples of suitable moieties that may be used in the creation of X include optionally substituted $C_1$-$C_{12}$alkyl, substituted $C_2$-$C_{12}$heteroalkyl, optionally substituted $C_3$-$C_{12}$cycloalkyl, optionally substituted $C_6$-$C_{18}$aryl, and optionally substituted $C_1$-$C_{18}$heteroaryl.

In some embodiments X is a group of the formula:

$$-(CH_2)_qCO(AA)_rNH(CH_2)_s-$$

wherein each AA is independently an amino acid group;

q is an integer selected from the group consisting of 1, 2, 3, 4, 5, 6, 7, and 8;

r is an integer selected from the group consisting of 0, 1, 2, 3, 4, 5, 6, 7, and 8;

s is an integer selected from the group consisting of 0, 1, 2, 3, 4, 5, 6, 7, and 8.

In some embodiments q is 1. In some embodiments q is 2. In some embodiments q is 3. In some embodiments q is 4. In some embodiments q is 5. In some embodiments q is 6. In some embodiments q is 7. In some embodiments q is 8.

In some embodiments r is 0. In some embodiments r is 1. In some embodiments r is 2. In some embodiments r is 3. In some embodiments r is 4. In some embodiments r is 5. In some embodiments r is 6. In some embodiments r is 7. In some embodiments r is 8.

In some embodiments s is 0. In some embodiments s is 1. In some embodiments s is 2. In some embodiments s is 3. In some embodiments s is 4. In some embodiments s is 5. In some embodiments s is 6. In some embodiments s is 7. In some embodiments s is 8.

In some embodiments the amino acid is a naturally occurring amino acid. In some embodiments the amino acid is a non-naturally occurring amino acid. In some embodiments the amino acid is selected from the group consisting of phenyl alanine, tyrosine, amino hexanoic acid and cysteine.

In some embodiments q is 3, r is o and s is 5. In these embodiments X is a group of the formula:

$$-(CH_2)_3CONH(CH_2)_5-$$

In some embodiments X is a group of the formula:

$$-(CH_2)_n-,$$

wherein optionally one or more of the $CH_2$ groups may be independently replaced by a heteroatomic group selected from S, O, P and $NR^3$ where $R^3$ is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl; and n is an integer selected from the group consisting of 1, 2, 3, 4, 5, 6, 7, 8, 9 and 10.

In some embodiments n is selected from the group consisting of 1, 2, 3, 4, and 5. In some embodiments n is 4. In some embodiments n is 3. In some embodiments n is 3. In some embodiments n is 1.

In some embodiments X is selected from the group consisting of $-CH_2-$, $-CH_2CH_2-$, $-CH_2CH_2CH_2-$, $-CH_2CH_2CH_2CH_2-$ and $-CH_2OCH_2-$.

In some embodiments X is $-(CH_2)-$. In some embodiments X is $-(CH_2)_2-$. In some embodiments X is $-(CH_2)_3-$. In some embodiments X is $-(CH_2)_4-$. In some embodiments X is $-(CH_2)_5-$. In some embodiments X is $-(CH_2)_6-$. In some embodiments X is $-(CH_2)_7-$. In some embodiments X is $-(CH_2)_8-$. In some embodiments X is $-(CH_2)_9-$. In some embodiments X is $-(CH_2)_{10}-$.

The compounds of formula (I) and formula (II) may include any of a number of nitrogen containing macrocyclic metal ligands.

In some embodiments the ligand (L) may be a tetraazamacrocycle based on the cyclam and cyclen framework. In some embodiments L is a nitrogen containing cage metal ligand. Cage ligands of this type are typically useful as they bind strongly to metal ions leading to a stable complex being formed.

In some embodiments L is a nitrogen containing cage metal ligand of the formula:

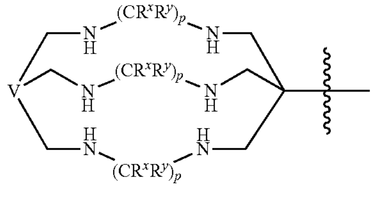

V is selected from the group consisting of N and $CR^4$;

each $R^x$ and $R^y$ are independently selected from the group consisting of H, $CH_3$, $CO_2H$, $NO_2$, $CH_2OH$, $H_2PO_4$, $HSO_3$, CN, $CONH_2$ and CHO;

each p is independently an integer selected from the group consisting of 2, 3, and 4;

$R^4$ is selected from the group consisting of H, OH, halogen, $NO_2$, $NH_2$, optionally substituted $C_1$-$C_{12}$alkyl, optionally substituted $C_6$-$C_{18}$aryl, cyano, $CO_2R^5$, $NHR^5$, $N(R^5)_2$ and a group of the formula:

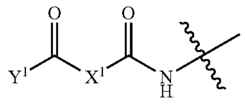

wherein:

$X^1$ is a linking moiety;

$Y^1$ is selected from the group consisting of $OR^6$, $SR^7$, $N(R^8)_2$ and a molecular recognition moiety;

wherein $R^5$ is H or $C_1$-$C_{12}$alkyl.

$R^6$ is selected from the group consisting of H, halogen, an oxygen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

$R^7$ is selected from the group consisting of H, halogen, a sulfur protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

each $R^8$ is independently selected from the group consisting of H, a nitrogen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl.

In some embodiments L is a macrocyclic metal ligand of the formula:

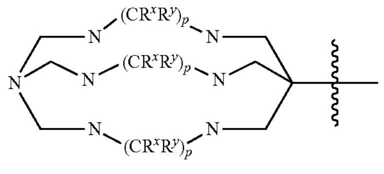

wherein $R^x$, $R^y$ and p are as defined above.

In some embodiments L is a macrocyclic ligand of the formula:

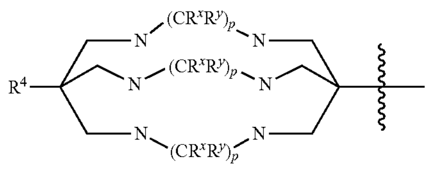

wherein $R^x$, $R^y$, $R^4$ and p are as defined above.

In some embodiments L is selected from the group consisting of:

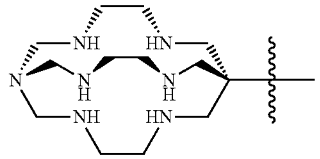

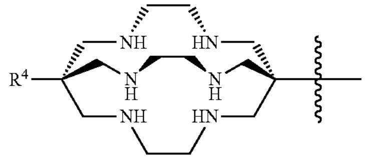

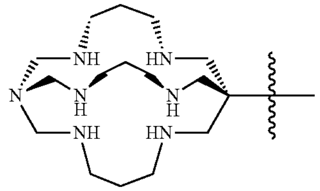

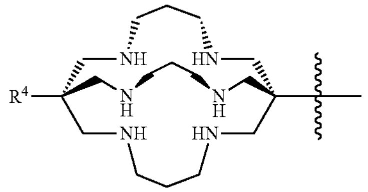

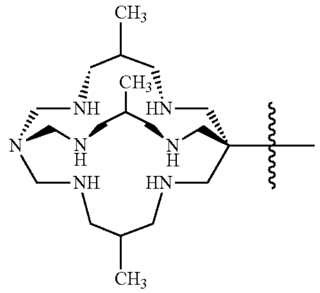

and

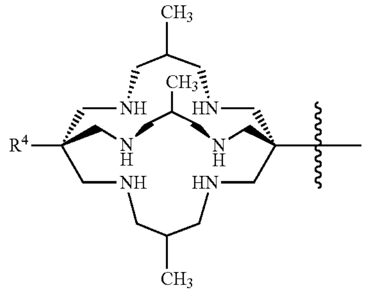

In some of the embodiments of the ligand L, the ligand is further functionalised or substituted by a group $R^4$. This allows for the formation of bi-functional ligands as there is the potential for the group $R^4$ to complement the existing functionality of the ligand or to provide additional functionality if required. In addition where one is trying to make a multimeric construct the group $R^4$ is typically the group used to introduce the second targeting or molecular recognition moiety.

In some embodiments $R^4$ is selected from the group consisting of $NH^2$, $CH_3$ and a group of the formula:

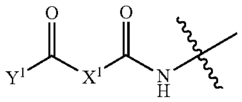

$X^1$ is a linking moiety;

$Y^1$ is selected from the group consisting of $OR^6$, $SR^7$, $N(R^8)_2$ and a molecular recognition moiety;

$R^6$ is selected from the group consisting of H, halogen, an oxygen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

$R^7$ is selected from the group consisting of H, halogen, a sulfur protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

each $R^8$ is independently selected from the group consisting of H, a nitrogen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl.

In some embodiments $X^1$ is a linking moiety having from 1 to 20 atoms in the normal chain. In some embodiments $X^1$ is a linking moiety having from 1 to 15 atoms in the normal chain. In some embodiments $X^1$ is a linking moiety having from 1 to 12 atoms in the normal chain. In some embodiments $X^1$ is a linking moiety having from 1 to 10 atoms in the normal chain. In some embodiments $X^1$ is a linking moiety having from 1 to 8 atoms in the normal chain. In some embodiments $X^1$ has 8 atoms in the normal chain. In some embodiments $X^1$ has 7 atoms in the normal chain. In some embodiments $X^1$ has 6 atoms in the normal chain. In some embodiments $X^1$ has 5 atoms in the normal chain. In some embodiments $X^1$ has 4 atoms in the normal chain. In some embodiments $X^1$ has 3 atoms in the normal chain. In some embodiments $X^1$ has 2 atoms in the normal chain. In some embodiments $X^1$ has 1 atom in the normal chain.

A wide range of possible moieties may be use to create a linking moiety of this type. Examples of suitable moieties that may be used in the creation of $X^1$ include optionally substituted $C_1$-$C_{12}$alkyl, substituted $C_2$-$C_{12}$heteroalkyl, optionally substituted $C_3$-$C_{12}$cycloalkyl, optionally substituted $C_6$-$C_{18}$aryl, and optionally substituted $C_1$-$C_{18}$heteroaryl.

In some embodiments $X^1$ is a group of the formula:

$$(CH_2)_tCO(AA)_uNH(CH_2)_v—$$

wherein each AA is independently an amino acid group;

t is an integer selected from the group consisting of 1, 2, 3, 4, 5, 6, 7, and 8;

u is an integer selected from the group consisting of 0, 1, 2, 3, 4, 5, 6, 7, and 8;

v is an integer selected from the group consisting of 0, 1, 2, 3, 4, 5, 6, 7, and 8.

In some embodiments t is 1. In some embodiments t is 2. In some embodiments t is 3. In some embodiments t is 4. In some embodiments t is 5. In some embodiments t is 6. In some embodiments t is 7. In some embodiments t is 8.

In some embodiments u is 0. In some embodiments u is 1. In some embodiments u is 2. In some embodiments u is 3. In some embodiments u is 4. In some embodiments u is 5. In some embodiments u is 6. In some embodiments u is 7. In some embodiments u is 8.

In some embodiments v is 0. In some embodiments v is 1. In some embodiments v is 2. In some embodiments v is 3. In some embodiments v is 4. In some embodiments v is 5. In some embodiments v is 6. In some embodiments v is 7. In some embodiments v is 8.

In some embodiments the amino acid is a naturally occurring amino acid. In some embodiments the amino acid is a non-naturally occurring amino acid. In some embodiments the amino acid is selected from the group consisting of phenyl alanine, tyrosine, amino hexanoic acid and cysteine.

In some embodiments t is 3, u is o and v is 5. In these embodiments $X^1$ is a group of the formula:

$$—(CH_2)_3CONH(CH_2)_5—$$

In some embodiments $X^1$ is a group of the formula $$—(CH_2)_a—,$$

wherein optionally one or more of the $CH_2$ groups may be independently replaced by a heteroatomic group selected from S, O, P and $NR^9$ where $R^9$ is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl;

a is an integer selected from the group consisting of 1, 2, 3, 4, 5, 6, 7, 8, 9 and 10.

In some embodiments a is selected from the group consisting of 1, 2, 3, 4, and 5. In some embodiments a is 4. In some embodiments n is 3. In some embodiments a is 2. In some embodiments a is 1.

In some embodiments $X^1$ is selected from the group consisting of $—CH_2—$, $—CH_2CH_2—$, $—CH_2CH_2CH_2—$, $—CH_2CH_2CH_2CH_2—$ and $—CH_2OCH_2—$.

In some embodiments $X^1$ is $—(CH_2)—$. In some embodiments $X^1$ is $—(CH_2)_2—$. In some embodiments $X_1$ is $—(CH_2)_3—$. In some embodiments $X^1$ is $—(CH_2)^4—$. In some embodiments $X^1$ is $—(CH_2)_5—$. In some embodiments $X^1$ is $—(CH_2)_6—$. In some embodiments $X^1$ is $—(CH_2)_7—$. In some embodiments $X^1$ is $—(CH_2)_8—$. In some embodiments $X^1$ is $—(CH_2)_9—$. In some embodiments $X^1$ is $—(CH_2)_{10}—$.

In some embodiments $Y^1$ is OH or a molecular recognition moiety. In some embodiments $Y^1$ is OH. In some embodiments $Y^1$ is a molecular recognition moiety.

In some embodiments L is a group of the formula:

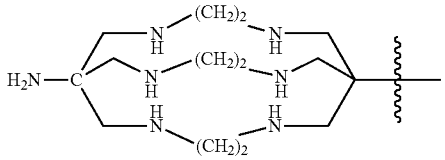

In some embodiments of the compounds of formula (I) Y is OH.

In the compounds of formula (II) Y is a molecular recognition moiety. In some embodiments of the compounds of both formula (I) and formula (II) $Y^1$ is a molecular recognition moiety.

In those embodiments where Y or $Y^1$ are a molecular recognition moiety it may be any moiety that has the ability to recognise a target moiety in a physiological environment. In some embodiments the molecular recognition moiety includes a molecular recognition portion which is directly attached to the remainder of the molecule. In some embodiments the molecular recognition moiety includes a spacer portion and a molecular recognition portion wherein the spacer portion joins the molecular recognition portion to the remainder of the molecule. The spacer may be any suitable construct and is typically chosen such that it provides a suitable distance or “space” between the ligand moiety of the molecule and the molecular recognition portion of the molecule. The exact length (if required at all) will vary depending upon the specific target receptor, the nature of the ligand and the nature of the molecular recognition portion. In some instances the spacer may be desirable as it allows for more facile synthesis of the compounds of the invention based on the nature of the molecular recognition portion.

In some embodiments the molecular recognition moiety or molecular recognition portion is selected from the group consisting of an antibody, a protein, a peptide, a carbohydrate, a nucleic acid, an oligonucleotide, an oligosaccharide and a liposome or a fragment or derivative thereof.

In some embodiments the molecular recognition moiety or molecular recognition portion is an antibody or a fragment or derivative thereof. In some embodiments the molecular recognition moiety is a protein or a fragment or derivative thereof. In some embodiments the molecular recognition moiety or molecular recognition portion is a peptide or a fragment or derivative thereof. In some embodiments the molecular recognition moiety or molecular recognition portion is a carbohydrate or a fragment or derivative thereof. In some embodiments the molecular recognition moiety or molecular recognition portion is a nucleic acid or a fragment or derivative thereof. In some embodiments the molecular recognition moiety or molecular recognition portion is an oligonucleotide or a fragment or derivative thereof. In some embodiments the molecular recognition moiety or molecular recognition portion is an oligosaccharide or a fragment or derivative thereof. In some embodiments the molecular recognition moiety or molecular recognition portion is folic acid or a fragment or derivative thereof. In some embodiments the molecular recognition moiety or molecular recognition portion is vitamin B12 or a fragment or a derivative thereof. In some embodiments the molecular recognition moiety or molecular recognition portion is a liposome or a fragment or a derivative thereof.

In some embodiments the molecular recognition moiety or molecular recognition portion is selected from the group consisting of Octreotate, octreotide, [$Tyr^3$]-octreotate, [Tyr1]-octreotate, bombesin, bombesin(7-14), gastrin releasing peptide, single amino acids, penetratin, annexin V, TAT, cyclic RGD, glucose, glucosamine (and extended carbohydrates), folic acid, neurotensin, neuropeptide Y, cholecystokinin (CCK) analogues, vasoactive intestinal peptide (VIP), substance P, and alpha-melanocyte-stimulating hormone (MSH).

In some embodiments the molecular recognition moiety or molecular recognition portion is selected from the group consisting of [$Tyr^3$]-octreotate and bombesin. In some embodiments the molecular recognition moiety is [$Tyr^3$]-octreotate. In some embodiments the molecular recognition moiety is $Lys^3$-bombesin. In some embodiments the molecular recognition moiety is cyclic RGD.

In some embodiments of the compounds of formula (I) or formula (II) the nitrogen containing macrocyclic metal ligand is complexed with a metal ion. The ligand may be complexed with any suitable metal ion and may be used to deliver a range of metal ions. In some embodiments the metal ion is selected from the group consisting of Cu, Tc, Gd, Ga, In, Co, Re, Fe, Au, Ag, Rh, Pt, Bi, Cr, W, Ni, V, Ir, Pt, Zn, Cd, Mn, Ru, Pd, Hg, and Ti.

In some embodiments the metal ion is a radionuclide selected from the group consisting of Cu, Tc, Ga, Co, In, Fe, and Ti. The present compounds have been found to be particularly applicable useful in binding copper ions. In some embodiments the metal ion is a radionuclide selected from the group consisting of $^{60}Cu$, $^{62}Cu$, $^{64}Cu$ and $^{67}Cu$. In some embodiments the metal ion is $^{60}Cu$. In some embodiments the metal ion is $^{62}Cu$. In some embodiments the metal ion is $^{64}Cu$. In some embodiments the metal ion is $^{67}Cu$.

The invention also relates to pharmaceutical compositions including a compound of the invention as described above and a pharmaceutically acceptable carrier, diluent or excipient.

In a further aspect there is provided method of producing a compound of formula (I), Formula (I)

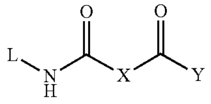

wherein L, X and Y are as defined above; the method including (a) reacting an amino substituted metal chelating ligand or a metal complex thereof of the formula:

$L\text{-}NH_2$ wherein L is a nitrogen containing macrocyclic metal ligand;

with an activated dicarbonyl compound; and (b) isolating the compound of formula (I) or a metal complex thereof.

The activated dicarbonyl compound used in the synthetic methods of the present invention may be any suitable dicarbonyl compound. In some embodiments the activated dicarbonyl compound is a compound of the formula (III):

Formula (III)

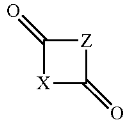

wherein X is as defined above and Z is O, S or $NR^2$.

In some embodiments the activated dicarbonyl compound is a compound of the formula (IV):

Formula (IV)

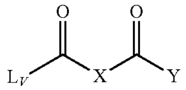

wherein X and Y are as defined above and $L_v$ is a leaving group.

The leaving group may be any suitable group that can be displaced by the desired incoming chemical moiety and a number of suitable leaving groups are well known in the art. In some embodiments the leaving group is selected from the group consisting of Cl, Br, $CH_3SO_3$, $CH_3C_6H_4SO_3$, and a group of the formula:

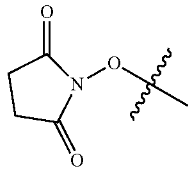 [SMILES: *ON1C(=O)CCC1=O]

The compounds may be reacted under a wide variety of reaction conditions suitable to facilitate the reaction. In some embodiments the amino substituted metal chelating ligand and the activated dicarbonyl compound are reacted in the presence of a base. A number of suitable bases may be used. In some embodiments the base is diisopropylethylamine.

In yet a further aspect there is provided a method of treating or preventing a condition in a subject, the method including the step of administering a therapeutically effective amount of a compound of formula (II) which is coordinated to a radionuclide to a subject. In some embodiments the condition is cancer.

In yet a further aspect there is provided a method of radioimaging a subject, the method including the step of administering an effective amount of a compound of formula (II) which is coordinated to a radionuclide to a subject.

These and other features of the present teachings are set forth herein.

DETAILED DESCRIPTION

In this specification a number of terms are used which are well known to a skilled addressee. Nevertheless for the purposes of clarity a number of terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. In certain embodiments the substituent groups are one or more groups independently selected from the group consisting of halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)$R^a$, —C(=O)O$R^a$, C(=O)N$R^aR^b$, C(=NOH)$R^a$, C(=N$R^a$)N$R^bR_c$, N$R^aR^b$, N$R^a$C(=O)$R^b$, N$R^a$C(=O)O$R^b$, N$R^a$C(=O)N$R^b$, $R^c$, N$R^a$C(=N$R^b$)N$a^cr^{ed}$, N$R^a$S$O_2R^b$, —S$R^a$, S$O_2$N$R^aR^b$, —O$R^a$, OC(=O)N$R^aR^b$, OC(=O)$R^a$ and acyl, wherein $R^a$, $R^b$, $R^c$ and $R^d$ are each independently selected from the group consisting of H, $C_1$-$C_{12}$alkyl, $C_1$-$C_{12}$haloalkyl, $C_2$-$C_{12}$alkenyl, $C_2$-$C_{12}$alkynyl, $C_2$-$C_{10}$ heteroalkyl, $C_3$-$C_{12}$cycloalkyl, $C_3$-$C_{12}$cycloalkenyl, $C_2$-$C_{12}$heterocycloalkyl, $C_2$-$C_{12}$ heterocycloalkenyl, $C_6$-$C_{18}$aryl, $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In some embodiments each optional substituent is independently selected from the group consisting of: halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, $CH_3$, $CH_2CH_3$, OH, $OCH_3$, $CF_3$, $OCF_3$, $NO_2$, $NH_2$, and CN.

As used herein the term "amino acid" refers to a molecule which contains both an amine and a carboxyl function. The amino acid may be a natural or an unnatural amino acid.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkyl" as a group or part of a group refers to a straight or branched aliphatic hydrocarbon group, preferably a $C_1$-$C_{12}$ alkyl, more preferably a $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group. Typically an aryl group is a $C_6$-$C_{18}$ aryl group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_9$ cycloalkyl group. The group may be a terminal group or a bridging group.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$ heteroaryl group. The group may be a terminal group or a bridging group.

A "leaving group" is a chemical group that is readily displaced by a desired incoming chemical moiety. Accordingly in any situation the choice of leaving group will depend upon the ability of the particular group to be displaced by the incoming chemical moiety. Suitable leaving groups are well known in the art, see for example "Advanced Organic Chemistry" Jerry March $4^{th}$ Edn. pp 351-357, Oak Wick and Sons NY (1997). Examples of suitable leaving groups include, but are not limited to, halogen, alkoxy (such as ethoxy, methoxy), sulphonyloxy, optionally substituted arylsulfonyl. Specific examples include chloro, iodo, bromo, fluoro, ethoxy, methoxy, methansulphonyl, triflate and the like.

The term "normal chain" refers to the direct chain joining the two ends of a linking moiety.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Additional information on pharmaceutically acceptable salts can be found in Remington's Pharmaceutical Sciences, 19th Edition, Mack Publishing Co., Easton, PA 1995. In the case of agents that are solids, it is understood by those skilled in the art that the inventive compounds, agents and salts may exist in different crystalline or polymorphic forms, all of which are intended to be within the scope of the present invention and specified formulae.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state. An effective amount for radioimaging is typically sufficient to identify the radionuclide in the subject.

The term "molecular recognition moiety" refers to an entity capable of binding to a particular molecular entity, typically a receptor location in the physiological environment. The term includes antibodies, proteins, peptides, carbohydrates, nucleic acids, oligonucleotides, oligosaccharides and liposomes.

The term "oxygen protecting group" means a group that can prevent the oxygen moiety reacting during further derivatisation of the protected compound and which can be readily removed when desired. In one embodiment the protecting group is removable in the physiological state by natural metabolic processes. Examples of oxygen protecting groups include acyl groups (such as acetyl), ethers (such as methoxy methyl ether (MOM), β-methoxy ethoxy methyl ether (MEM), p-methoxy benzyl ether (PMB), methylthio methyl ether, Pivaloyl (Piv), Tetrahydropyran (THP)), andsilyl ethers (such as Trimethylsilyl (TMS) tert-butyl dimethyl silyl (TBDMS) and triisopropylsilyl (TIPS).

The term "nitrogen protecting group" means a group that can prevent the nitrogen moiety reacting during further derivatisation of the protected compound and which can be readily removed when desired. In one embodiment the protecting group is removable in the physiological state by natural metabolic processes and in essence the protected compound is acting as a prodrug for the active unprotected species. Examples of suitable nitrogen protecting groups that may be used include formyl, trityl, phthalimido, acetyl, trichloroacetyl, chloroacetyl, bromoacetyl, iodoacetyl; urethane-type blocking groups such as benzyloxycarbonyl ('CBz'), 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl ('tBoc'), 2-(4-xenyl)-isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxy-carbonyl, cyclo-pentanyloxy-carbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfono)-ethoxycarbonyl, 2-(methylsulfono)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalymethoxy carbonyl, 4-acetoxybenzyloxycarbonyl, 2,2,2-trichloroethoxycarbonyl, 2-ethynyl-2-propoxycarbonyl, cyclopropylmethoxycarbonyl, 4-(decycloxy)benzyloxycarbonyl, isobornyloxycarbonyl, 1-piperidyloxycarbonlyl and the like; benzoylmethylsulfono group, 2-nitrophenylsulfenyl, diphenylphosphine oxide, and the like. The actual nitrogen protecting group employed is not critical so long as the derivatised nitrogen group is stable to the condition of subsequent reaction(s) and can be selectively removed as required without substantially disrupting the remainder of the molecule including any other nitrogen protecting group(s). Further examples of these groups are found in: Greene, T. W. and Wuts, P. G. M., Protective Groups in Organic Synthesis, Second edition; Wiley-Interscience: 1991; Chapter 7; McOmie, J. F. W. (ed.), Protective Groups in Organic Chemistry, Plenum Press, 1973; and Kocienski, P. J., Protecting Groups, Second Edition, Theime Medical Pub., 2000.

The compounds of the invention as discussed above may include a wide variety of nitrogen containing macrocyclic metal ligands.

The ligand may be a monocyclic nitrogen containing metal ligand based on the cyclam or cyclen frameworks. Ligand of this type and derivatives thereof may be synthesised using methodology available in the art such as in Bernhardt (J. Chem. Soc., Dalton Transactions, 1996, pages 4319-4324), Bernhardt et al (J. Chem. Soc., Dalton Transactions, 1996, pages 4325-4330), and Bernhardt and Sharpe (Inorg Chem, 2000, 39, pages 2020-2025). Various other ligands of this general type may be made by variation of the procedures described in these articles.

The ligand may also be a cage like cryptand ligand as described for example in Geue (Chemical communications, 1994, page 667). Cryptand ligands of this type are described in U.S. Pat. No. 4,497,737 in the name of Sargeson et al, the disclosure of which is incorporated herein by reference.

The synthesis involves a metal ion template reaction and involves condensation of a tris-(diamine) metal ion complex (see column 3 lines 30 to 35) with formaldehyde and an appropriate nucleophile in the presence of base. The identity of the nucleophile will determine the identity of the substituents on the cage ligand and a skilled addressee can access a wide variety of substitution patterns around the cage ligand by judicious choice of the appropriate amine used in the condensation as well as the identity of the nucleophile.

In order to produce the compounds of formula (I) of the invention the amino substituted ligand or a metal complexed form thereof is reacted with an appropriate dicarbonyl compound under suitable reaction conditions to arrive at the final product.

Whilst the reaction may be performed on the free ligand there is still a possibility of the reaction being compromised by the presence of the ring nitrogen(s). As such it is desirable to perform the reaction using a metal complex thereof as the metal serves to act as a protecting group for the secondary nitrogen atoms in the ring.

The reaction may be carried out in any suitable solvent which is inert to the two reactants with the identity of the solvent being determined by the relative solubilities of the anhydride and the amine substituted metal ligand. Examples of solvents that may be used include aliphatic, aromatic, or halogenated hydrocarbons such as benzene, toluene, xylenes; chlorobenzene, chloroform, methylene chloride, ethylene chloride; ethers and ethereal compounds such as dialkyl ether, ethylene glycol mono or -dialkyl ether, THF, dioxane; nitriles such as acetonitrile or 2-methoxypropionitrile; N, N-dialkylated amides such as dimethylformamide; and dimethyl acetamide, dimethylsulphoxide, tetramethylurea; as well as mixtures of these solvents with each other.

The reaction may be carried out at any of a number of suitable temperatures with the reaction temperature being able to be readily determined on a case by case basis. Nevertheless the reaction temperature is typically carried out at from 0 to 100° C., more typically 50 to 80° C.

The reaction may be carried out using a wide variety of activated dicarbonyl compounds. In some embodiments the activated dicarbonyl compound is an anhydride of the formula:

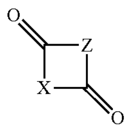

wherein X is as defined above and Z is O, S or $NR^2$.

Anhydride compounds of this type are generally readily available for certain values of X and thus these compounds may be readily used for values of X for which they are obtainable. It is desirable that they be utilised where possible as the potential for side reactions is reduced somewhat with these compounds.

In some embodiments the activated dicarbonyl compound is a compound of the formula:

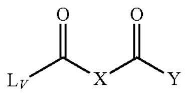

wherein X and Y are as defined above and Ly is a leaving group. The $L_v$ group on the compounds of this type may be any suitable leaving group but is typically selected from the group consisting of Cl, Br, $CH_3SO_3$, $CH_3C_6H_4SO_3$, and a group of the formula:

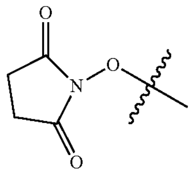 [SMILES: *ON1C(=O)CCC1=O]

In choosing a suitable leaving group for reactions of this type the skilled worker in the art will have regard for the functionality of the remainder of the molecule and the ease of production of the activated dicarbonyl compound in each instance.

The reaction is also typically carried out in the presence of a base as this is found to facilitate the reaction. Examples of suitable bases include hindered tertiary amines with trialkyl amines such as trimethylamine, triethyleneamine, diisopropylethyl amine being suitable examples of bases for use in the reaction. The amount of base used is such that it is in a significant molar excess so as to ensure that the reaction does not become affected by acidification as it progresses.

The exact compound produced will depend upon the reaction stoichiometry and the starting materials with a skilled addressee being able to adjust either of these variables to produce the desired final product.

In addition it is desired that the linker X be extended to be significantly longer than the compounds readily accessible by the route detailed above it is possible to elaborate the carboxy group (such as by standard peptide chemistry techniques) to introduce further amino acid groups to the chain. The methods of achieving reactions of this type are well within the skill of a skilled addressee in the area.

Examples of compounds of formula (I) that may be produced using the methodology described above include:

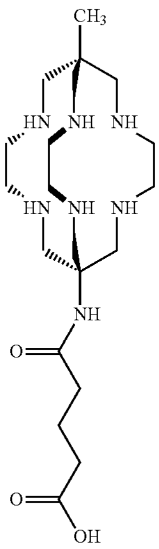
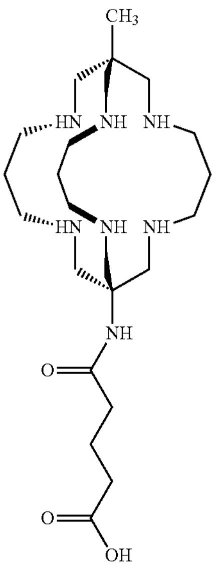
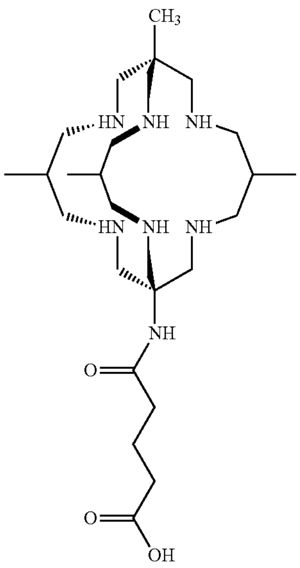
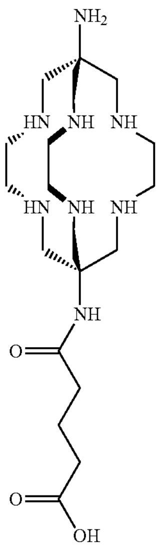
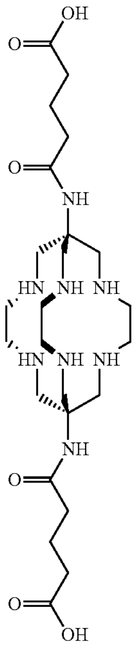
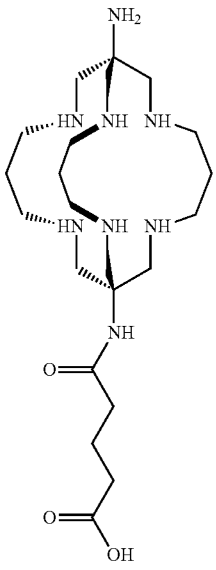
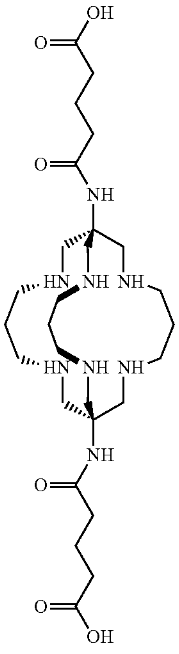
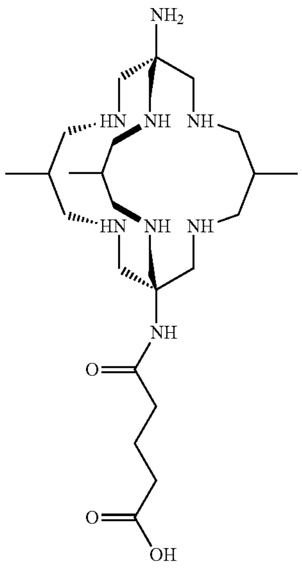
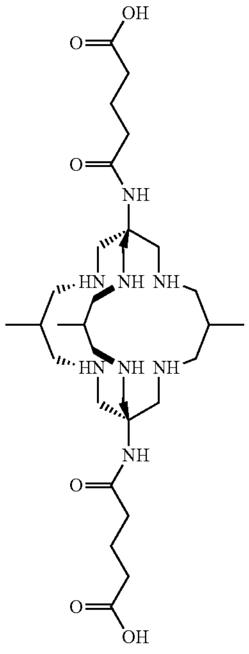
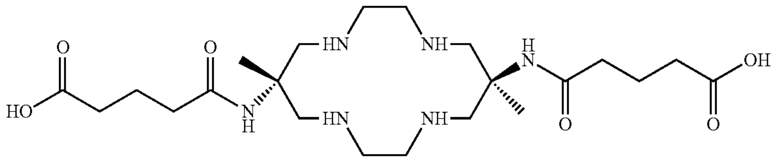 and -continued

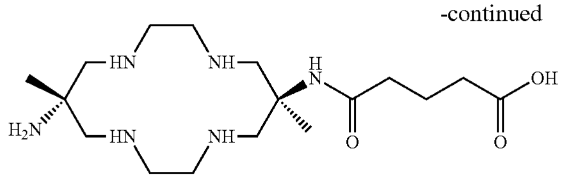

or a metal complex thereof.

These compounds may then be further elaborated to produce compounds of formula (II) which contain a molecular recognition moiety by reaction of the carboxyl terminus (or an activated form thereof) with a suitable reactive element on a molecular recognition moiety under suitable coupling conditions. An example of such a reaction would be one in which a coupling between the carboxyl portion of the compound formula (I) is conducted with the N termini of a peptide or protein (such as the N-terminus of a biologically active peptide) to form a peptide linkage such that the metal ligand becomes bound (via the linker) to the molecular recognition unit.

Alternatively the molecules of formula (I) may be reacted with molecules to introduce a 'spacer moiety" prior to addition of the molecular recognition portion of the molecular recognition moiety. Thus for example the compounds of formula (I) may be functionalised, for example through the carboxyl moiety to form one or more peptidic linkages to produce as a synthetic intermediate a compound of formula (I) with a spacer moiety attached (the spacer moiety forming part of the molecular recognition moiety in the final compound). Examples of compounds of this type include:

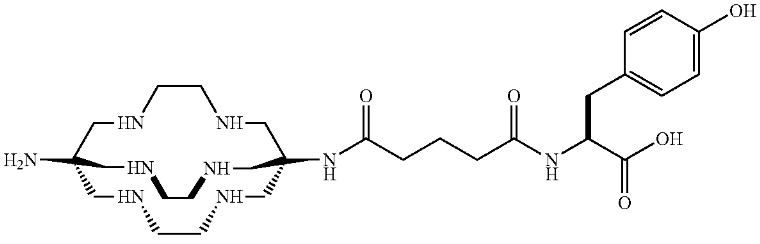

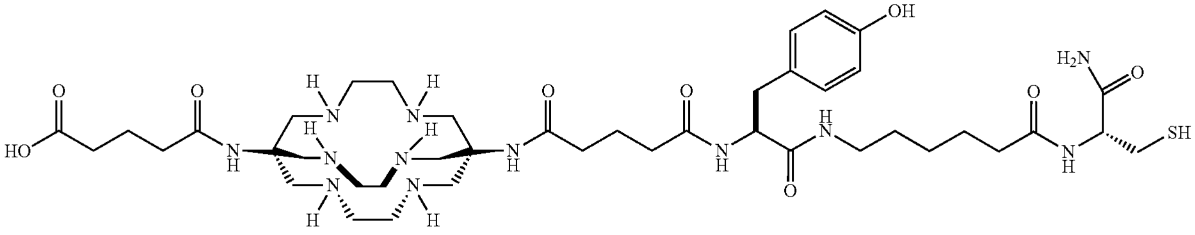

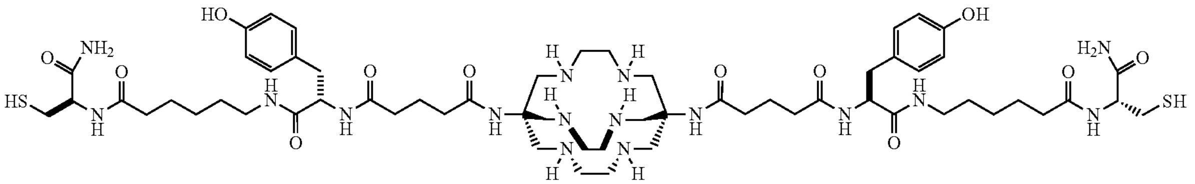

As can be seen in each of these compounds the compound of formula (I) has been elaborated by addition of a 'spacer moiety". In the first compound a tyrosine moiety has been added to one side of the molecule. In the second compound the peptide Tyr-aHX-Cys-$NH_2$ has been added to one side of the molecule and in the third compound the peptide Tyr-aHX-Cys-$NH_2$ has been added to both sides of the molecule.

As stated above the compound of formula (I) or intermediate compounds as discussed above may then be further elaborated by addition of a molecular recognition moiety (or molecular recognition portion) as the case may be to form compounds of formula (II).

Examples of compounds of formula (II) include:
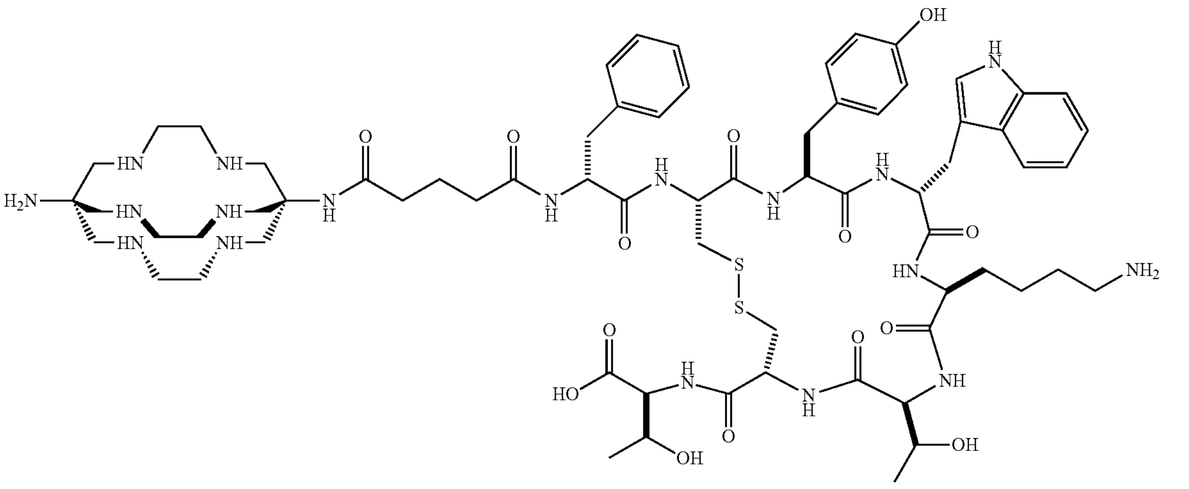
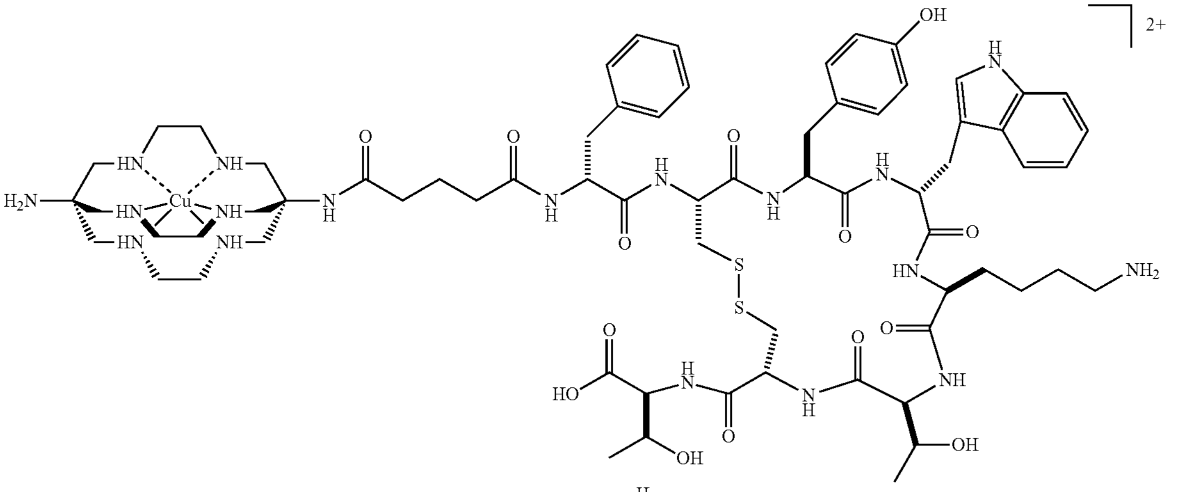
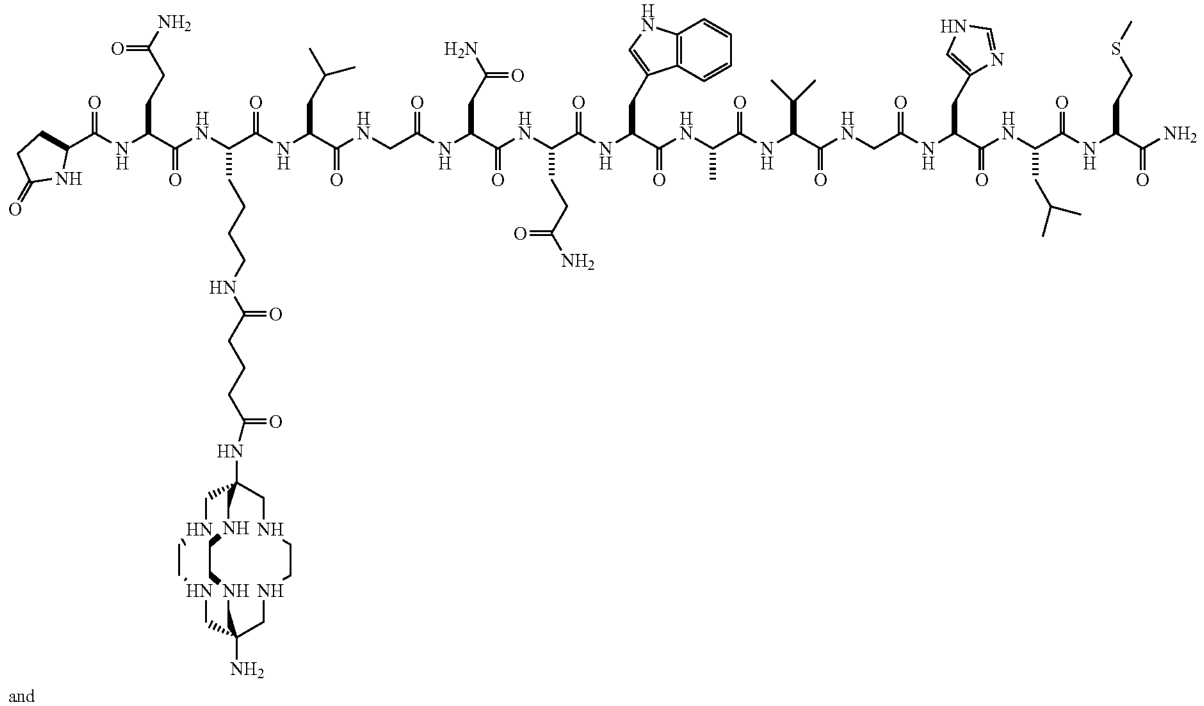
and -continued

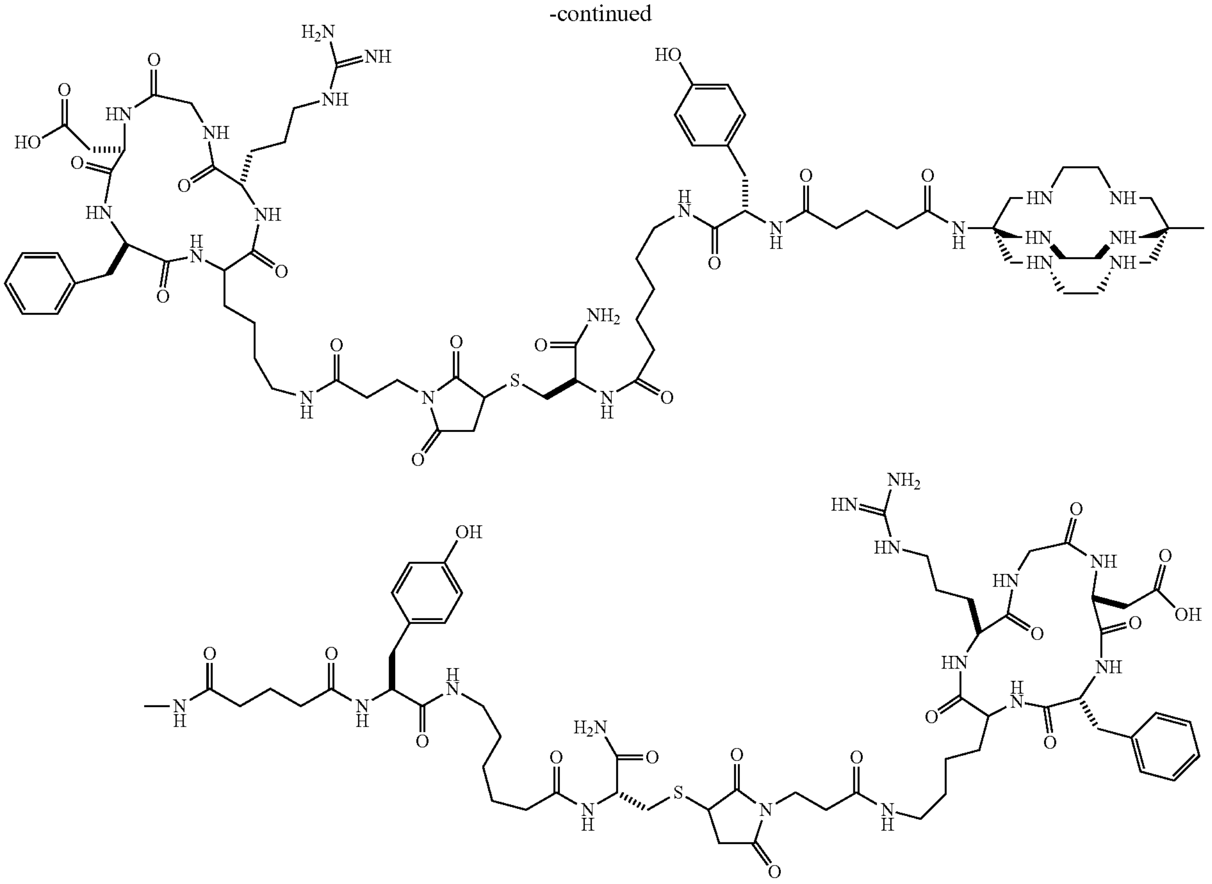

In principle any of a wide range of biologically active molecular recognition units may be employed in the present application with the only limitation being that the molecular recognition moiety used must contain a functionality capable of being bound (either directly or through a spacer) to the compound of formula (I). Whilst a number of different functional groups may be contemplated (such as the maleimido propionate group on RGDfK above which couples with a thiol moiety) the molecular recognition moiety preferably has an N terminus for coupling through the carboxyl residue of the compound of the invention as discussed above. The coupling reactions may be carried out in ways well known in the art and employ peptide synthesis techniques well known in the art which may involve either solid phase or liquid phase peptide synthesis techniques to be used. In some instances the nitrogen atoms of the ligand may be protected prior to peptide coupling using standard nitrogen protecting groups in order to facilitate smooth coupling. If this is done any suitable nitrogen protecting group may be used with the N-tert-butoxy carbonyl group (t-boc) being found to be particularly useful.

Upon completion the protective groups may be removed using techniques well known in the art.

The formation of the metal complexes of the compounds synthesised in this way is carried out using techniques well known in the art.

As discussed above the compounds of the invention are useful as they either have, or can be modified to contain a molecular recognition moiety. The compounds of formula (II) containing a radionuclide complexed with the ligand may be used in either radiotherapy or in diagnostic imaging applications. In each instance both therapy and diagnostic imaging will rely on the molecular recognition moiety being involved in facilitating the localisation of the complex containing the radionuclide in the desired tissues or organs of the subject being treated/imaged.

Thus for example in relation to the use of the radiolabelled compounds of formula (II) it is anticipated that these will be used by administration of an effective amount of the radiolabelled compound to a subject followed by monitoring of the subject after a suitable time period to determine if the radiolabelled compound has localised at a particular location in the body or whether the compound is broadly speaking evenly distributed through the body. As a general rule where the radio labelled compound is localised in tissue or an organ of the body this is indicative of the presence in that tissue or organ of something that is recognised by the particular molecular recognition moiety used.

Accordingly judicious selection of a molecular recognition moiety or molecular recognition portion is important in determining the efficacy of any of the radiolabelled compounds of the invention in diagnostic imaging applications. In this regard a wide range of molecular recognition moieties or molecular recognition portions are known in the art which are well characterised and which are known to selectively target certain receptors in the body. In particular a number of molecular recognition moieties or molecular recognition portions are known that target tissue or organs when the patient is suffering from certain medical conditions. Examples of molecular recognition moieties or molecular recognition portions that are known and may be used in this invention include Octreotate, octreotide, [$Tyr^3$]- octreotate, [$Tyr^1$]-octreotate, bombesin, bombesin(7-14), gastrin releasing peptide, single amino acids, penetratin, annexin V, TAT, cyclic RGD, glucose, glucosamine (and extended carbohydrates), folic acid, neurotensin, neuropeptide Y, cholecystokinin (CCK) analogues, vasoactive intestinal peptide (VIP), substance P, alpha-melanocyte-stimulating hormone (MSH). For example, certain cancers are known to over express somatostatin receptors and so the molecular recognition moiety may be one which targets these receptors. An example of a molecular recognition moieties or molecular recognition portions of this type is [$Tyr^3$]-octreotate. Another example of a molecular recognition moieties or molecular recognition portions is cyclic RGD which is an integrin targeting cyclic peptide. In other examples a suitable molecular recognition moieties or molecular recognition portions is bombesin which is known to target breast and pancreatic cancers.

The monitoring of the subject for the location of the radiolabelled material will typically provide the analyst with information regarding the location of the radiolabelled material and hence the location of any material that is targeted by the molecular recognition moiety (such as cancerous tissue). An effective amount of the compounds of the invention will depend upon a number of factors and will of necessity involve a balance between the amount of radioactivity required to achieve the desired radio imaging effect and the general interest in not exposing the subject (or their tissues or organs) to any unnecessary levels of radiation which may be harmful.

The methods of treatment of the present invention involve administration of a compound of formula (II) complexed to a radionuclide. The compounds of formula (II) contain a molecular recognition moiety in order to deliver the radionuclide to the desired location in the body where its mode of action is desired. As discussed above examples of such molecular recognition moieties are known in the art and a skilled artisan can select the appropriate molecular recognition moiety to target the desired tissue in the body to be treated.

A therapeutically effective amount can be readily determined by an attending clinician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular radio labelled compound administered, the mode of administration, the bioavailability of the preparation administered, the dose regime selected, the use of other medications and other relevant circumstances.

In addition the treatment regime will typically involve a number of cycles of radiation treatment with the cycles being continued until such time as the condition has been ameliorated. Once again the optimal number of cycles and the spacing between each treatment cycle will depend upon a number of factors such as the severity of the condition being treated, the health (or lack thereof) of the subject being treated and their reaction to radiotherapy. In general the optimal dosage amount and the optimal treatment regime can be readily determined by a skilled addressee in the art using well known techniques.

In using the compounds of the invention they can be administered in any form or mode which makes the compound available for the desired application (imaging or radio therapy). One skilled in the art of preparing formulations of this type can readily select the proper form and mode of administration depending upon the particular characteristics of the compound selected, the condition to be treated, the stage of the condition to be treated and other relevant circumstances. We refer the reader to Remingtons Pharmaceutical Sciences, 19th edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found at least one container having a unit dosage of the agent(s). Conveniently, in the kits, single dosages can be provided in sterile vials so that the clinician can employ the vials directly, where the vials will have the desired amount and concentration of compound and radio nucleotide which may be admixed prior to use. Associated with such container(s) can be various written materials such as instructions for use, or a notice in the form prescribed by a governmental agency regulating the manufacture, use or sale of pharmaceuticals, imaging agents or biological products, which notice reflects approval by the agency of manufacture, use or sale for human administration.

The compounds of the invention may be used or administered in combination with one or more additional drug(s) that are anti-cancer drugs and/or procedures (e.g. surgery, radiotherapy) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs that include anti-cancer drugs, the compounds of the invention may be used in a combination therapy. When this is done the compounds are typically administered in combination with each other. Thus one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

If desired, and for more effective distribution, the compounds can be incorporated into slow release or targeted delivery systems such as polymer matrices, liposomes, and microspheres.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

As discussed above, the compounds of the embodiments may be useful for treating and/or detecting proliferative diseases. Examples of such cell proliferative diseases or conditions include cancer (include any metastases), psoriasis, and smooth muscle cell proliferative disorders such as restenosis. The compounds of the present invention may be particularly useful for treating and/or detecting tumours such as breast cancer, colon cancer, lung cancer, ovarian cancer, prostate cancer, head and/or neck cancer, or renal, gastric, pancreatic cancer and brain cancer as well as hematologic malignancies such as lymphoma and leukaemia. In addition, the compounds of the present invention may be useful for treating and/or detecting a proliferative disease that is refractory to the treatment and/or detecting with other anti-cancer drugs; and for treating and/or detecting hyperproliferative conditions such as leukaemia's, psoriasis and restenosis. In other embodiments, compounds of this invention can be used to treat and/or detect pre-cancer conditions or hyperplasia including familial adenomatous polyposis, colonic adenomatous polyps, myeloid dysplasia, endometrial dysplasia, endometrial hyperplasia with atypia, cervical dysplasia, vaginal intraepithelial neoplasia, benign prostatic hyperplasia, papillomas of the larynx, actinic and solar keratosis, seborrheic keratosis and keratoacanthoma.

Synthesis of Compounds of the Invention

The agents of the various embodiments may be prepared using the reaction routes and synthesis schemes as described below, employing the techniques available in the art using starting materials that are readily available. The preparation of particular compounds of the embodiments is described in detail in the following examples, but the artisan will recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, $3^{rd}$ Edition, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

General Synthetic Scheme

Scheme 1 is a general synthetic scheme outlining the procedures for the manufacture of compounds of the invention of general formula (I). This general procedure can be modified to produce other compounds of the invention with different linking moieties X of the cyclic dicarbonyl (III) by appropriate modification of the starting materials and reagents used. A skilled addressee would readily be able to make these changes.

As can be seen in scheme 1 an appropriately nitrogen containing macrocyclic ligand (V) (which may or may not be complexed with a metal) is reacted with a suitable cyclic dicarbonyl (III) containing a desired linking moiety X under basic conditions to provide the dicarbonyl metal chelating agent (I). The dicarbonyl metal chelating agent (I) has a functional group Y for further conjugation with a suitable molecular recognition moiety.

Scheme 1

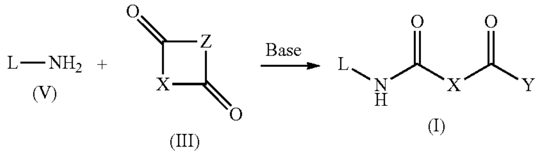

(V) (III) (I)

This scheme outlines a synthesis wherein Z is an oxygen or sulfur atom or a group of formula $NR^2$. When Z is an oxygen atom, a terminal carboxylic acid handle is formed for further elaboration. Alternatively, when Z is a sulfur atom, a terminal carboxylic thiol is formed for further elaboration by methods well known in the art. When Z is $NR^2$ the terminal amide is formed. The scheme may be modified to produce compounds within the scope of the present disclosure in which the cyclic dicarbonyl (III) may also act as a base in the reaction shown above. Other variations to arrive at the desired final product is within the skill of a skilled addressee in the art.

Scheme 2 demonstrates an alternative synthesis of the compounds of the invention. As shown in scheme 2 an alternative synthesis involves the provision of a suitably activated linear dicarbonyl compound in which one of the carbonyl moieties has been activated by providing the carbonyl with a suitable leaving group. This is reacted with eth amine compound under suitable reaction conditions leading to displacement of the leaving group and formation of the desired final product.

Scheme 2

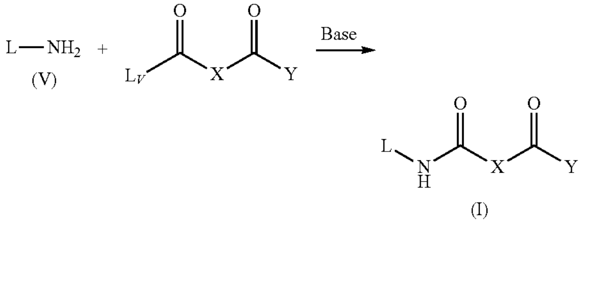

(V) (I)

The nitrogen containing macrocyclic metal chelating ligand L for use in the syntheses described above can be any of a range of macrocyclic metal ligands known in the art as discussed above. In the schemes above the metal ligand can be reacted with the anhydride in free form or be bound to a metal ion thereby deactivating the nucleophilicity of the heteroatoms in the macrocycle prior to reaction. One example of such a metal chelator is 1,8-$(NH_2)_2$sar. 1,8-$(NH_2)_2$sar can coordinate with a metal ion to substantially deactivate the six secondary amines in the macrocycle and thereby selectively allowing the two “free” primary amines to react.

The compounds of formula (II) may be produced from the compounds of formula one using standard peptide coupling techniques in which the carboxy termini of the compounds of formula (I) is reacted with the amine terminus of a molecular recognition moiety under standard conditions to produce the coupled product.

Synthetic procedures for the synthesis of selected compounds of formula (I) are detailed below.

EXAMPLES

In the examples described below, unless otherwise indicated, all temperatures in the following description are in degrees Celsius and all parts and percentages are by weight, unless indicated otherwise.

Various starting materials and other reagents were purchased from commercial suppliers, such as Aldrich Chemical Company or Lancaster Synthesis Ltd., and used without further purification, unless otherwise indicated. Tetrahydrofuran (THF) and N,N-dimethylformamide (DMF) were purchased from Aldrich in SureSeal bottles and used as received. All solvents were purified by using standard methods in the art, unless otherwise indicated. SP Sephadex C25 and DOWEX 50wx2 200-400 mesh cation exchange resin was purchased from Aldrich. Fmoc-L-amino acids, HATU, HCTU and 2-chlorotrityl resin were purchased from GL Biochem Ltd (Shanghai, China).

Fmoc-Lys(iv-Dde)-OH and Fmoc-D-amino acids were purchased from Bachem AG (Switzerland). Fmoc-Pal-PEG-PS resin was purchased from Applied Biosystems (Foster City, California). Nova PEG Rink Amide resin was purchased from NovaBiochem, Darmstadt, Germany. [Co($(NO_2)_2$sar)]$Cl_3$, [Co($(NH_2)_2$sar)]$Cl_3$, $(NH_2)_2$sar, [Cu $(NH_3)_2$sar]$(CF_3SO_3)_4$ were prepared according to established procedures. (1) Geue, R. J.; Hambley, T. W.; Harrowfield, J. M.; Sargeson, A. M.; Snow, M. R. *J. Am. Chem. Soc.* 1984, 106, 5478-5488. (2) Bottomley, G. A.; Clark, I. J.; Creaser, I. I.; Engelhardt, L. M.; Geue, R. J.; Hagen, K. S.; Harrowfield, J. M.; Lawrance, G. A.; Lay, P. A.; Sargeson, A. M.; See, A. J.; Skelton, B. W.; White, A. H.; Wilner, F. R. *Aust. J. Chem.* 1994, 47, 143-179 and (3) Bernhardt, P. V.; Bramley, R.; Engelhardt, L. M.; Harrowfield, J. M.; Hockless, D. C. R.; Korybut-Daszkiewicz, B. R.; Krausz, E. R.; Morgan, T.; Sargeson, A. M.; Skelton, B. W.; White, A. H. *Inorg. Chem.* 1995, 34, 3589-3599.

The reactions set forth below were performed under a positive pressure of nitrogen, argon or with a drying tube, at ambient temperature (unless otherwise stated), in anhydrous solvents, and the reaction flasks are fitted with rubber septa for the introduction of substrates and reagents via syringe. Glassware was oven-dried and/or heat-dried.

Work-ups were typically done by doubling the reaction volume with the reaction solvent or extraction solvent and then washing with the indicated aqueous solutions using 25% by volume of the extraction volume (unless otherwise indicated). Product solutions were dried over anhydrous sodium sulfate prior to filtration, and evaporation of the solvents was under reduced pressure on a rotary evaporator and noted as solvents removed in vacuo. Flash column chromatography [Still et al, J. Org. Chem., 43, 2923 (1978)] was conducted using E Merck-grade flash silica gel (47-61 mm) and a silica gel:crude material ratio of about 20:1 to 50:1, unless otherwise stated.

Hydrogenolysis was done at the pressure indicated or at ambient pressure.

Mass spectra were recorded in the positive ion mode on an Agilent 6510 Q-TOF LC/MS Mass Spectrometer coupled to an Agilent 1100 LC system (Agilent, Palo Alto, CA). Data were acquired and reference mass corrected via a dual-spray electrospray ionisation source, using the factory-defined calibration procedure. Each scan or data point on the Total Ion Chromatogram is an average of 9652 transients, producing 1.02 scans $s^{-1}$. Spectra were created by averaging the scans across each peak. Mass spectrometer conditions: fragmentor: 200-300 V; drying gas flow: 7 L/min; nebuliser: 30 psi; drying gas temp: 325° C.; Vhd cap: 4000 V; skimmer: 65 V; OCT $R_f$V: 750 V; scan range acquired: 150-3000 m/z.

HPLC-MS traces were recorded using an Agilent Eclipse Plus C18 column (5 μm, 2.1×150 mm) coupled to the Agilent 6510 Q-TOF LC/MS Mass Spectrometer described above. 1 μL aliquots of each sample were injected onto the column using the Agilent 1100 LC system, with a flow rate of 0.5 mL/min. Data acquisition parameters are the same as those described above for mass spectra, with the exception of the fragmentor (fragmentor voltage: 100 V).

NMR spectra were recorded on a Varian FT-NMR 500 spectrometer operating at 500 MHz for $^1$H NMR and 125.7 MHz for $^{13}$C-NMR. NMR spectra are obtained as $D_2O$ solutions (reported in ppm), using acetone as the reference standard (2.22 ppm and 30.89 ppm respectively). Other NMR solvents were used as needed. When peak multiplicities are reported, the following abbreviations are used: s=singlet, d=doublet, t=triplet, m=multiplet, br=broadened, dd=doublet of doublets, dt=doublet of triplets. Coupling constants, when given, are reported in Hertz.

Semi-preparative HPLC purifications were performed using an Agilent 1200 Series HPLC system with a 5 mL/min flow rate. Solvent gradients and column specifications are described in the examples. An automated Agilent 1200 fraction collector collected 1-3 mL fractions and fraction collection was based on UV-Vis detection at 214 or 220 nm, with a lower threshold limit between 100-400 mAU. Each fraction was analysed using MS and analytical HPLC.

Analytical HPLC traces were acquired using an Agilent 1200 Series HPLC system and an Agilent Zorbax Eclipse XDB-C18 column (4.6×150 mm, 5 μm) with a 1 mL/min flow rate and UV spectroscopic detection at 214 nm, 220 nm and 270 nm.

V-Vis spectra were acquired on a Cary 300 Bio UV-Vis spectrophotometer, from 800-200 nm at 0.500 nm data intervals with a 300.00 nm/min scan rate.

Voltametric experiments were performed with an Autolab (Eco Chemie, Utrecht, Netherlands) computer-controlled electrochemical workstation. A standard three-electrode arrangement was used with a glassy carbon disk (d, 3 mm) as working electrode, a Pt wire as auxiliary electrode and a Ag/AgCl reference electrode (silver wire in $H_2O$ (KCl (0.1 M) $AgNO_3$ (0.01 M)). Scan rate: 100 mV/s, sample interval: 1.06 mV, sensitivity: $1\times10^{-4}$ A.

HPLC traces of radiolabelled peptides were acquired using a Waters Comosil C18 column (4.6×150 mm) coupled to a Shimadzu LC-20AT with a sodium iodide scintillation detector and a UV-Vis detector. 100 μL aliquots of each radiolabelled sample were injected onto the column, using a flow rate of 1 mL/min.

The following examples are intended to illustrate the embodiments disclosed and are not to be construed as being limitations thereto. Additional compounds, other than those described below, may be prepared using the following described reaction scheme or appropriate variations or modifications thereof.

Example 1

$[Cu((1\text{-}NH_3)(8\text{-}NHCO(CH_2)_3COOH)Sar)](NO_3)_3$ (Also Called $[CuL^1](NO_3)_3$) and $[Cu(1,8\text{-}NHCO(CH_2)_3COOH)_2Sar](CF_3SO_3)Cl$ (Also Called $[CuL^{2}](CF_3SO_3)Cl$)

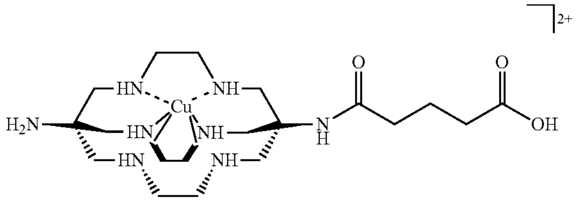

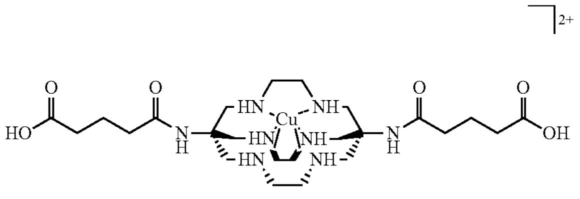

A solution of $[Cu(NH_3)_2Sar](CF_3SO_3)_4$ (1.5 g, 1.53 mmol) in anhydrous N,N-dimethylacetamide (12 mL) was heated under an atmosphere of nitrogen to 70° C. Glutaric anhydride (0.19 g, 1.64 mmol) and diisopropylethylamine (600 μL) were added and the solution was heated at 70° C. for two hours. The solution was cooled and water (20 mL) was added. The solution was applied to a column of SP Sephadex C-25 cation exchange ($Na^+$ form, 30×5 cm). The column was eluted with 0.05 M sodium citrate solution to separate three components. (Chromatographic yield: Fraction 1~40%, fraction 2~40%, fraction 3~20%.) Each fraction was applied separately to a DOWEX 50 W×2 cation exchange column ($H^+$ form, 10×5 cm). The column was washed with water (500 mL) and 1 M HCl solution (500 mL) and then eluted with 4 M 20) HCl (350 mL) and the eluent was evaporated to dryness under reduced pressure at 40° C. Fraction 1: $[Cu(1,8\text{-}NHCO(CH_2)_3COOH)_2Sar]Cl_2$.xHCl (1.00 g) MS: $[CuC_{24}H_{45}N_8O_6]^+$ m/z=604.2732 (experimental), 604.2764 (calculated). Fraction 2: $[Cu(1\text{-}NH_4)(8\text{-}NHCO(CH_2)_3COOH)Sar]Cl_3$.xHCl (0.82 g) MS: $[CuC_{19}H_{39}N_8O_3]^+$ m/z=490.2439 (experimental), 490.2447 (calculated). The dark blue residue from fraction 2 was dissolved in distilled water (30 mL). Concentrated nitric acid (2 mL) was added and the solution was concentrated by rotary evaporation until crystallisation commenced. The mixture was cooled at 5° C. for 30 mins before the light blue crystals were collected by filtration. $[Cu(1\text{-}NH_4)(8\text{-}NHCO(CH_2)_3COOH)Sar](NO_3)_3$: 0.13 g, 13% isolated yield.

Crystals suitable for X-ray diffraction were grown from evaporation of a solution of $[Cu(1\text{-}NH_3)(8\text{-}NHCO(CH_2)_3COOH)Sar]Cl_3$.xHCl (20 mg) in ~1 M $HNO_3$ (2 mL) at ambient temperature.

Crystals of $[Cu(1,8\text{-}NHCO(CH_2)_3COOH)_2Sar](CF_3SO_3)Cl$ were suitable for X-ray diffraction studies and were formed as follows: $[Cu(1,8\text{-}NHCO(CH_2)_3COOH)_2Sar]Cl_2$.xHCl (0.45 g) was dissolved in water (2 mL) and a solution of silver triflate (0.33 g in 2 mL water) was added. This solution was filtered twice (MilliQ syringe filter (0.45 μm)) and evaporated to dryness under reduced pressure to give a dark blue-purple residue. The residue was redissolved in water (8 mL) and over the course of 10 min, blue crystals precipitated from this solution. These were collected and dried by filtration. $Cu(1,8\text{-}NHCO(CH_2)_3COOH)_2Sar](CF_3SO_3)Cl$: 0.13 g. Crystals suitable for X-ray diffraction were grown from evaporation of a solution of $Cu(1,8\text{-}NHCO(CH_2)_3COOH)_2Sar](CF_3SO_3)Cl$ (30 mg) in water (6 mL) at ambient temperature.

Crystal data: $[CuL^1](NO_3)_3$ $C_{25}H_{41}N_{11}O_{12}Cu$, M=679.17, T=130.0(2) K, λ□=0.71069, monoclinic, space group $P2_1/c$ a=8.345(5) b=12.231(5), c=26.941(5) Å, b=93.658(5)°, V=2744(2) $Å^3$, Z=4, $D_c$=1.644 mg $M^{-3}$ μ(Mo-Kα) 0.879 $mm^{-1}$, F(000)=1428, crystal size 0.35×0.3×0.01 mm. 17656 reflections measured, 6107 independent reflections ($R_{int}$=0.17), the final R was 0.067 [l>2□(l)] and wR($F^2$) was 0.1524. $[CuL^2](CF_3SO_3)Cl$ $C_{19}H_{46}ClCuF_3N_8O_9S$, M=790.75, T=130.0(2) K, λ□=0.71069, orthorhombic, space group $C222_1$ a=12.4608(13) b=20.445(2), c=13.2263 (14) Å, V=3369.6(6) $Å^3$, Z=4, $D_c$=1.559 mg $M^{-3}$ μ(Mo-Kα) 0.879 $mm^{-1}$, F(000)=1652, crystal size 0.40×0.30×0.20 mm. 8848 reflections measured, 2973 independent reflections ($R_{int}$=0.0334), the final R was 0.0542 [l>2σ(l)] and wR($F^2$) was 0.1471. Structures obtained and solved by Assoc. Prof. Jonathan M. White.

Microanalysis: $[CuL^1](NO_3)_3$: $CuC_{19}H_{41}N_{11}O_{12}$—C 34.86%, H 6.40%, N 24.76% (experimental); —C 33.60%, H 6.08%, N 22.69% (calculated); $[CuL^2](CF^3SO^3)Cl$: $CuC_{25}H_{46}N_8O_9SClF_3$—C 38.06%, H 5.92%, N 14.20%, S 3.88% (experimental); —C 37.97%, H 5.86%, N 14.17%, S 4.06% (calculated).

UV-vis: $[Cu(1\text{-}NH_4)(8\text{-}NHCO(CH_2)_3COOH)Sar](NO_3)_3$ in water, pH 4, $\lambda_{max}$=658 nm, ε=140 $M^{-1}$ $cm^{-1}$; $[Cu(1,8\text{-}NHCO(CH_2)_3COOH)_2Sar](CF_3SO_3)Cl$ in water, pH=4, $\lambda_{max}$=655 nm, ε=146 $M^-cm^{-1}$ Electrochemistry: $[Cu(1\text{-}NH_4)(8\text{-}NHCO(CH_2)_3COOH)Sar](NO_3)_3$ (1 mM) in an aqueous solution of $NaBF_4$ (100 mM), pH3.5, $E_{red}$=−1.086 (vs $[Fe(CN)_6]^{3-/4-}$, E°=0).

Example 2

$(1\text{-}NH_3Cl)(8\text{-}NHCO(CH_2)_3COOH)Sar$: (Also Called $L^1$·HCl)

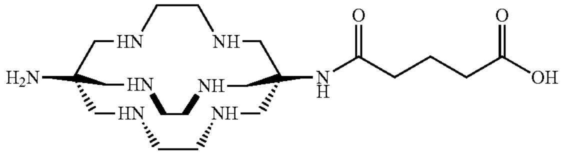

A solution of $[Cu(1\text{-}NH_3)(8\text{-}NHCO(CH_2)_3COOH)Sar]Cl_3$.xHCl (0.44 g, ~0.73 mmol based on x=0) in water (4 mL) was deoxygenated by purging with $N_2$ gas for 20 mins. Sodium sulfide (0.6 g) was added and the solution was stirred overnight at room temperature (under an atmosphere of nitrogen gas). After addition of sodium sulfide, the solution turned a dark green. After ~16 hours, a black-brown precipitate was present and the solution appeared a light yellow-green. This mixture was filtered (Whatman Filter Paper 1) and the filtrate diluted with 1 M HCl (250 mL) resulting in the formation of a cloudy, white precipitate. The mixture was filtered (MilliQ syringe filters (0.45 μm)) and applied to a DOWEX 50 W×2 cation exchange column ($H^+$ form, 10×5 cm). The column was washed with 1 M HCl solution (750 mL) (to remove $Na_2S$) and then eluted with 4 M HCl solution (400 mL). The eluent was evaporated to dryness under reduced pressure to give a clear residue with a slight blue tinge. Because this residue was still slightly blue, the above process was repeated. The final solution was evaporated to dryness to give a clear, colourless residue. $(1\text{-}NH_3Cl(8\text{-}NHCO(CH_2)_3COOH)Sar$.xHCl: 0.30 g, 89% MS: $[C_{19}H_{40}N_8O_3]^+$ 429.3372 (experimental), 429.3296 (calculated). $^1H$ NMR: δ 1.852, m, 2H, $\beta CH_2$ (with respect to COOH); 2.358, t, $^3J$=7.54, 2H, glutarate $CH_2$; 2.417, t, $^3J$=7.18, 2H glutarate $CH_2$; 3.181, broad s, 6H, cage $CH_2$; 3.315, broad s, 12H, cage $CH_2$; 3.694, broad s, 6H, cage $CH_2$. $^{13}C$ NMR: δ 20.36, 33.46, 35.54 (glutarate $CH_2$); 46.46, 48.39, 50.66, 51.18, 55.23, 56.54 (cage); 177.937, 178.516 (CO).

Example 3

$(8\text{-}NHCO(CH_2)_3COOH)(x\text{-}NCO_2\text{-}t\text{-}Bu)_{4.5}Sar$: (Also Called $L^1$-$(t\text{-}Boc)_{3\text{-}5}$)

$(1\text{-}NH_3Cl)(8\text{-}NHCO(CH_2)_3COOH)Sar$.xHCl was converted to a trifluoromethanesulfonate salt to increase its solubility in N,N-dimethylacetamide. In brief, $(1\text{-}NH_4Cl)(8\text{-}NHCO(CH_2)_3COOH)Sar$.xHCl (0.20 g, 0.43 mmol) was dissolved in water (5 mL) and silver triflate (0.11 g, 0.43 mmol) was added, precipitating silver chloride. The solution was filtered (MilliQ 0.45 μm syringe filter) and evaporated to dryness under reduced pressure to give a colourless, clear hydroscopic residue. $(1\text{-}NH_4CF_3SO_3)(8\text{-}NHCO(CH_2)_3COOH)Sar.xH_2O$: 0.31 g.

$(1\text{-}NH_3CF_3SO_3)(8\text{-}NHCO(CH_2)_3COOH)Sar.xH_2O$ (80 mg, 0.138 mmol based on x=0) was dissolved in a solution of N,N-dimethylacetamide:water (4:1) (10 mL). Di-tert-butyldicarbonate (0.25 g, 1.15 mmol) and diisopropylethylamine (100 μL) were added and the solution was stirred under an atmosphere of nitrogen gas for 30 min. After this time, the solvent was removed under high vacuum at ~40° C. The residue was dissolved in acetonitrile (15 mL), filtered (MilliQ 0.45 μm syringe filter) and lyophilised to remove traces of N,N-dimethylacetamide. Once the crude compound was dry, it was dissolved in a solution of A:B (70:30) (A=milliQ water containing 0.1% trifluoroacetic acid, B=acetonitrile containing 0.1% trifluoroacetic acid) (5 mL), filtered (MilliQ 0.45) μm syringe filter), and applied to a C18 cartridge (Alltech Maxi-Clean C18 900 mg). The cartridge was washed sequentially with 5 mL A, 5 mL 10% B in A and 5 mL 20% B in A. It was then eluted with 5 mL 80% B in A, and 1 mL fractions were collected. Most of the desired compound (>95%) was collected in the first two fractions. These were lyophilised to yield a mixture of t-BOC protected isomers, and the degree of protection ranged from 3-5 t-BOC groups per molecule of cage compound. $(8\text{-}NHCO(CH_2)_3COOH)(x\text{-}NCOO\text{-}t\text{-}Bu)_{4.5}Sar$: 30 mg, 25% yield. MS: $[C_{19}H_{41}N_8O_3(C_5H_8O_2)_3]^+$729.4879 (experimental), 729.4869 (calculated); $[C_{19}H_{41}N_8O_3(C_5H_8O_2)_4]^+$829.5414 (experimental), 829.5414 (calculated); $[C_{19}H_{41}N_8O_3(C_5H_8O_2)_5]^+$929.5942 (experimental), 929.5918 (calculated).

Example 4

(1,8-NHCO($CH_2$)$_3$COOH)$_2$Sar: (Also Called $L^2$)

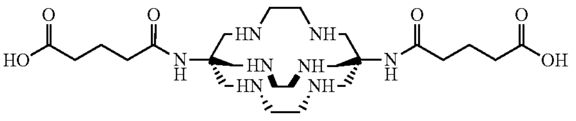

A solution of [Cu(1,8-NHCO($CH_2$)$_3$COOH)$_2$Sar] $Cl_2$.xHCl (1.0 g, ~1.48 mmol based on x=0) in water (20 mL) was deoxygenated by purging with $N_2$ gas for 20 mins. Sodium sulfide (1.3 g) was added and the solution was stirred overnight at room temperature (under an atmosphere of nitrogen gas). After ~16 hours, the solution was green with a black-brown precipitate. Another portion of sodium sulfide (1.4 g) was added and the solution stirred overnight at room temperature. After this time, the solution appeared light yellow. This mixture was filtered (Whatman Filter Paper 1) and the filtrate diluted with 1 M HCl (250 mL) resulting in the formation of a cloudy, white precipitate. The mixture was filtered (MilliQ syringe filters (0.45 μm)) and applied to a DOWEX 50W×2 cation exchange column ($H^+$ form, 10×5 cm). The column was washed with 1 M HCl solution (750 mL) (to remove $Na_2S$) and then eluted with 4 M HCl solution (400 mL). The eluent was evaporated to dryness under reduced pressure to give a clear, colourless residue. (1,8-NHCO($CH_2$)$_3$COOH)$_2$Sar.xHCl: 0.255 g, 32% MS: $[C_{24}H_{47}N_8O_6]^+$ 543.3686 (experimental), 534.3619 (calculated). $^1H$ NMR: δ 1.856, m, 4H, β$CH_2$ (with respect to COOH); 2.336, t, $^3J$=7.47, 4H, glutarate $CH_2$; 2.411, t, $^3J$=7.19, 4H glutarate $CH_2$; 3.210, broad s, 12H, cage $CH_2$; 3.439, broad s, 12H, cage $CH_2$; $^{13}C$ NMR: δ 20.65, 33.43, 35.46 (glutarate $CH_2$); 47.40, 51.44. 56.23 (cage); 177.80, 178.44 (CO).

Example 5 $L^2$-(t-Boc)$_4$ $L^2$.xHCl (0.17 g, 0.31 mmol based on x=0) was dissolved in water (3 mL). Di-tert-butyldicarbonate (1 g, ~20 equivalents) in acetonitrile (7 mL) and triethylamine (0.5 mL) were added. The acetonitrile phase was not miscible with the aqueous phase, but the reaction was stirred vigorously under an inert atmosphere of nitrogen gas for 2 hours. After this time, the solvent was removed under reduced pressure and the remaining residue was dried under high vacuum at 45° C. for 2 hours. The dried residue was redissolved in a solution of A:B (90:10), filtered (MilliQ 0.45 μm syringe filter), and applied to a C18 cartridge (Alltech Maxi-Clean C18 900 mg). The cartridge was washed sequentially with 5 mL A and 5 mL 20% B in A. It was then eluted with 5 mL 50% B in A. This fraction was lyophilised to yield mainly $L^2$-(t-Boc)$_4$. $L^1$-(t-Boc)$_{3-5}$: 30 mg, 10% yield. MS: $[C_{44}H79N_8O_{14}]^+$943.68 (experimental), 943.57 (calculated);

Example 6

Sar-octreotate ($L^1$-$Tyr^3$-Octreotate)

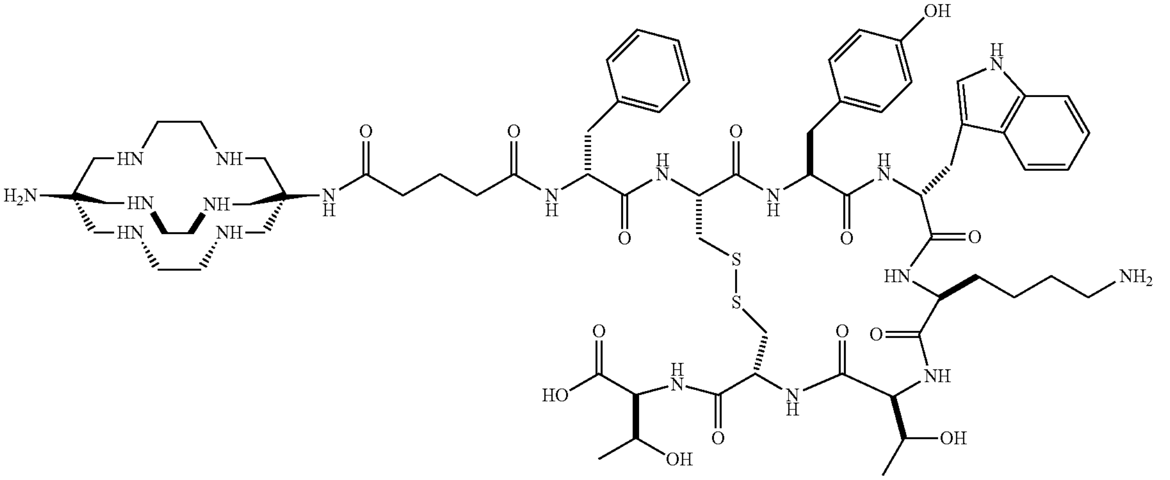

Linear [$Tyr^3$]-octreotate (linear OCT) peptide (dPhe-Cys-Tyr-dTrp-Lys-Thr-Cys-Thr-OH (Seq ID No:1) was synthesised on 2-chlorotrityl chloride resin using standard Fmoc solid phase peptide synthesis procedures. An excess of resin (0.06 g, ~0.8 mmol/g) was swelled in N,N-dimethylformamide (DMF). L1-(t-Boc)$_{3-5}$ (25 mg, 0.03 mmol), HCTU (20 mg, 0.05 mmol) and diisopropylethylamine (20 μL) in DMF (1 mL) were added to the resin and the mixture was stirred and left to react overnight. The reaction supernatant was then drained and the resin washed with DMF (3×5 mL) and dichloromethane (DCM) (3×5 mL). The resin was transferred to a falcon tube and trifluoroacetic acid (5 mL), deionised water (0.15 mL) and triisopropylsilane (0.15 mL) were added. The falcon tube was placed on a shaker for 40 min. The peptide material was precipitated from the solution using diethyl ether (15 mL) and the mixture was centrifuged (3 mins, 3000 rpm). The supernatant was discarded and the precipitate dissolved in A:B (70:30). This solution was filtered (MilliQ 0.45 μm syringe filter) and lyophilised.

The crude peptide material was purified by semi-preparative reverse phase HPLC (Eclipse XDB-C18 5 μm 9.5×250 mm column) using a linear 1% A→B/min gradient. Linear $L^1$-$Tyr^3$-octreotate eluted at 30 min (determined by ESI-MS) and fractions containing linear $L^1$-$Tyr^3$-octreotate were lyophilised. The dried fractions were then redissolved in ammonium acetate (25 mM, pH 6.5, 8 mL) and an excess of 2,2-dithiodipyridine (12 mg) was added. The solution was then applied to a semi-preparative reverse phase HPLC column, and purified using a linear 1% A→B/min gradient. Cyclic L[1]-Tyr[3]-octreotate eluted at 30 min and fractions containing cyclic L[1]-Tyr[3]-octreotate were lyophilised. L[1]-Tyr[3]-octreotate: 1-2 mg; HPLC retention time: 12.99 min (linear gradient, 0→60% B in A over 25 min); MS: $[C_{68}H105N18O_{14}S_2]^{3+}$ 487.25 (experimental), 487.25 (calculated); $[C_{68}H_{104}N_{18}O_{14}S_2]^{2+}$ 730.37 (calculated), 730.37 (experimental).

Example 7

CuSar-octreotate (Cu L[1]-Tyr[3]-Octreotate)

mmol), HCTU (20 mg, 0.05 mmol) and diisopropylethylamine (20 μL) in DMF (1 mL) were added to the resin and the mixture was stirred and left to react for 40 min. The reaction supernatant was then drained and the resin washed with dimethylformamide (3×5 mL) and dichloromethane (3×5 mL). The resin was transferred to a falcon tube and trifluoroacetic acid (5 mL), distilled water (0.15 mL) and triisopropylsilane (0.15 mL) were added. The falcon tube was placed on a shaker for 40 min. The peptide material was precipitated from the solution using diethyl ether (15 mL) and the mixture was centrifuged (3 min, 3000 rpm). The supernatant was discarded and the precipitate dissolved in A:B (70:30). This solution was filtered (MilliQ 0.45 μm syringe filter) and lyophilised to give pale blue material.

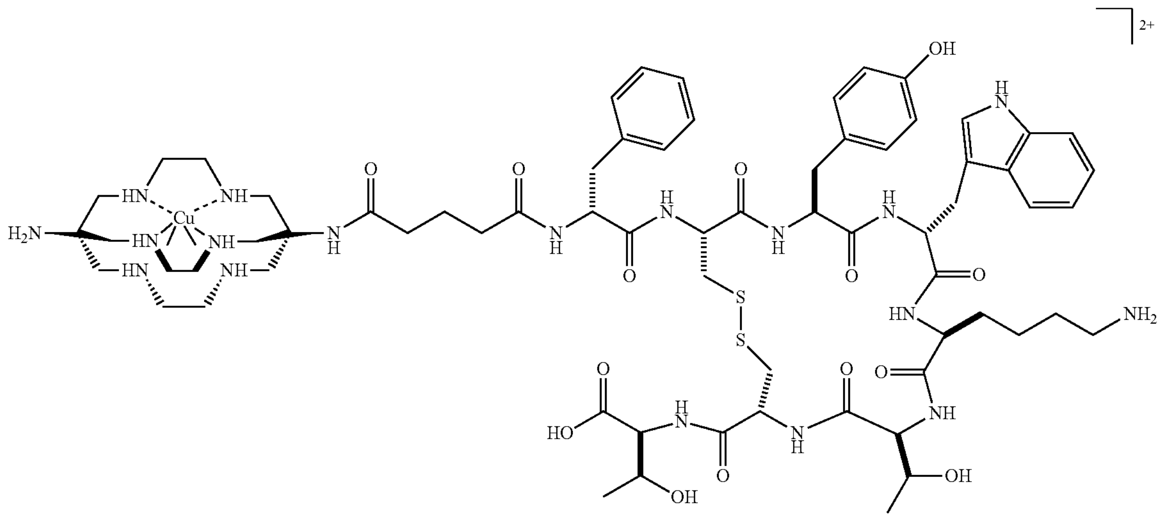

$[Cu(1\text{-}NH_4)(8\text{-}NHCO(CH_2)_3COOH)Sar]Cl_3 \cdot xHCl$ was converted to a trifluoromethanesulfonate salt to increase its solubility in N,N-dimethylacetamide. In brief, $[Cu(1\text{-}NH_3)(8\text{-}NHCO(CH_2)_3COOH)Sar]$Cl3.xHCl (0.14 g, 0.23 mmol) was dissolved in water (5 mL) and silver triflate (0.18 g, 0.70 mmol) was added, precipitating silver chloride. The solution was filtered (MilliQ 0.45 μm syringe filter) and evaporated to dryness under reduced pressure to give a sticky, blue hydroscopic residue. $[Cu(1\text{-}NH_3)(8\text{-}NHCO(CH_2)_3COOH)Sar](CF_3SO_3)_3.xH_2O$: 0.21 g.

Linear octreotate peptide on resin (0.10 g, ~0.8 mmol/g) was swelled in dimethylformamide. $Cu(1\text{-}NH_4)(8\text{-}NHCO(CH_2)_3COOH)Sar](CF_3SO_3)_3$ (30 mg, 0.03 mmol), HCTU (40 mg, 0.1 mmol) and diisopropylethylamine (40 μL) in DMF (1 mL) were added to the resin and the mixture was stirred and left to react for 3 hr. The reaction supernatant was then drained and the resin washed with dimethylformamide (3×5 mL). A second coupling was performed. $Cu(1\text{-}NH_4)(8\text{-}NHCO(CH_2)_3COOH)Sar](CF_3SO_3)_3$ (10 mg, 0.01

The crude peptide material was purified by semi-preparative reverse phase HPLC (Eclipse XDB-C18 5 μm 9.5×250 mm column) using a linear 1% A→B/min gradient. Linear CuSar-octreotate eluted at 30 min (determined by MS) and fractions containing linear CuSar-octreotate were lyophilised. The dried fractions were then redissolved in 25 mM ammonium acetate (8 mL) and an excess of 2,2-dithiodipyridine (12 mg) was added to form an intramolecular disulfide bond, cyclizing the octreotate. This solution was then applied to a semi-preparative reverse phase HPLC column, and purified using a linear 1% A→B/min gradient. Cyclic CuSar-octreotate eluted at 31.5 min and fractions containing cyclic CuSar-octreotate were lyophilised to give a light blue pellets. $CuSar\text{-}NHCO(CH_2)_3CO$-octreotate: 4 mg; HPLC retention time: 12.049 min (linear gradient, 0→60% B in A over 25 min). MS: $[CuC_{68}H_{102}N_{18}O_{14}S_2]^{2+}$: 760.8296 (experimental), 760.8280 (calculated); $[CuC_{68}H_{101}N_{18}O_{14}S_2]^{2+}$: 1520.6513 (experimental), 1520.6482 (calculated).

Example 8

Sar-Lys3-BBN: (Also Called $L^1$-$Lys_3$-BBN)

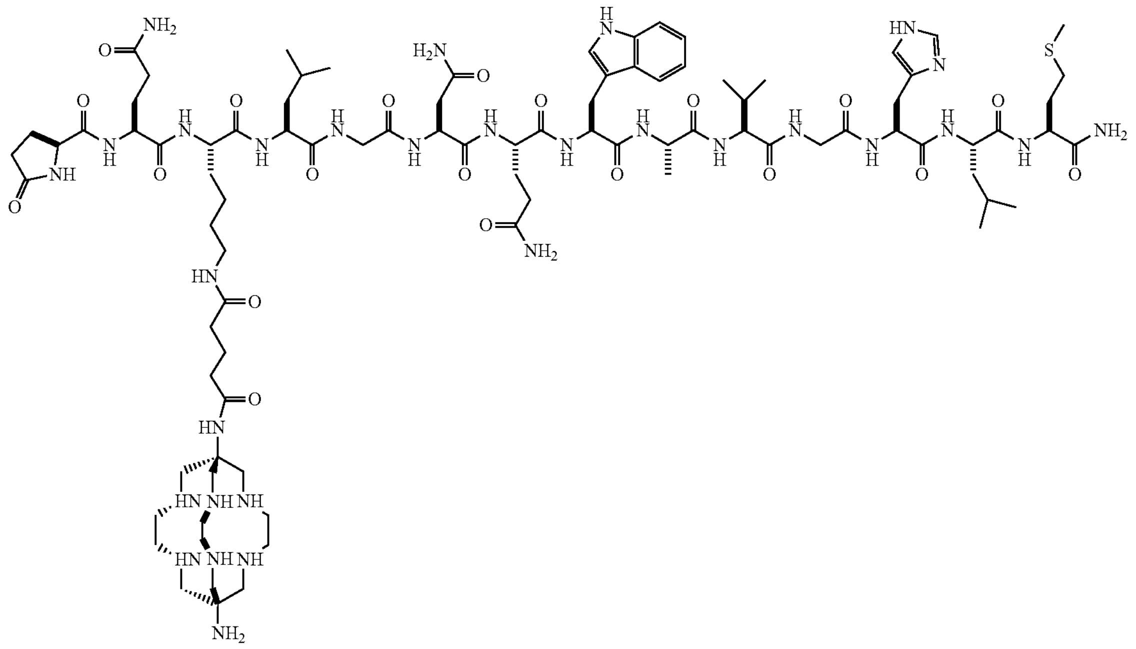

Bombesin peptide (BBN) (1-14) (Pyr-Gln-Lys-Leu-Gly-Asn-Gln-Trp-Ala-Val-Gly-His-Leu-Met-$NH_2$ (Seq ID No:2)) was synthesised on Fmoc-PAL-PEG-PS resin using standard Fmoc solid phase peptide synthesis procedures. The side chain of the $Lys^3$ residue was protected with a iv iv-Dde (Ne-1-(4,4-dimethyl-2,6-residue was protected with dioxocyclohexylidene)ethyl) group. This was selectively deprotected using 5% hydrazine in DMF (3×5 mL) over one hour. Resin (0.05 g, ~0.2 mmol/g) was swelled in DMF. $L^1$-$(t\text{-Boc})_{3\text{-}5}$ (10 mg, 0.012 mmol), HATU (10 mg, 0.026 mmol) and diisopropylethylamine (20 μL) in DMF (1 mL) were added to the resin and the mixture was stirred and left to react for 3 hrs. The reaction supernatant was then drained and the resin washed with DMF (3×5 mL) and DCM (3×5 mL). The resin was transferred to a falcon tube and trifluoroacetic acid (2 mL), deionised water (70 μL) and triisopropylsilane (70 μL) were added. This solution was placed on a shaker for 40 min. The solvent was evaporated under a stream of $N_2$ gas and the residue dissolved in A:B (70:30). This solution was filtered (MilliQ 0.45 μm syringe filter) and lyophilised.

The crude peptide material was purified by semi-preparative reverse phase HPLC (Phenomenex Synergi 4u Hydro-RP 80A 50 x21.20 mm), using a "slow" linear gradient (0.5% A→B/min). $L^1$-$Lys_3$-bombesin eluted with 25% B in A and fractions containing $L^1$-$Lys_3$-bombesin were lyophilised. The peptide was not pure, so the dried fractions were redissolved in milliQ water and applied to the same semi-preparative reverse phase HPLC column, and purified using a "very slow" linear 0.25% A→B/min gradient. $L^1$-$Lys_3$-bombesin eluted with ~26.5% B in A. An impurity with a lower molecular mass (~780) still persisted in these fractions, so the peptide was purified by semi-preparative reverse HPLC (Eclipse XDB-C18 5 μm 9.5×250 mm column) using a using a "slow" linear gradient (0.5% A→B/min). $L^1$-$Lys_3$-bombesin eluted with 26% B in A and fractions containing $L^1$-$Lys_3$-bombesin were lyophilised. Analytical reverse phase HPLC indicated that the final fractions contained 95% $L^1$-$Lys_3$-bombesin. $L^1$-$Lys_3$-bombesin: 1-50 μg; HPLC retention time: 13.59 min (linear gradient, 0→60% B in A over 25 min); MS: $[C_{90}H_{152}N_{30}O_{20}S_2]^{4+}$: 501.54 (experimental), 501.54 (calculated); $[C_{90}H_{151}N_{30}O_{20}S_2]^{3+}$: 668.39 (experimental), 668.38 (calculated); $[C_{90}H_{150}N_{30}O_{20}S_2]^{2+}$: 1002.07 (experimental), 1002.07 (calculated).

Example 9 $L^1$-Tyr

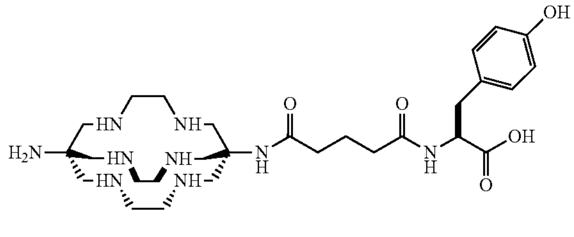

Fmoc-Tyr(tBu)-OH was coupled to 2-chlorotrityl resin (~1.3 mmol/g) using standard coupling procedures. The Fmoc protecting group was removed using 50% piperidine in DMF and the resin was washed with DMF (3×5 mL). Tyr resin (0.08 g) was swelled in DMF (0.5 mL). $L^1$-$(t\text{-Boc})_{3\text{-}5}$ (12 mg, 0.014 mmol), HATU (10 mg, 0.026 mmol) and diisopropylethylamine (10 μL) in DMF (1 mL) were added to the resin and the mixture was stirred and left to react for 2 hrs. The reaction supernatant was then drained and the resin washed with DMF (3×5 mL) and DCM (3×5 mL). The resin was transferred to a falcon tube and trifluoroacetic acid (2 mL), deionised water (70 μL) and triisopropylsilane (70 μL) were added. This solution was placed on a shaker for 40 min. The solvent was evaporated under a stream of $N_2$ gas and the residue dissolved in A:B (70:30). This solution was filtered (MilliQ 0.45 μm syringe filter) and lyophilised.

The crude peptide material was purified by semi-preparative reverse phase HPLC (Eclipse XDB-C18 5 μm 9.5×250 mm column) using a linear 1% A→B/min gradient. $L^1$-Tyr eluted with 13% B in A (determined by ESI-MS) and fractions containing $L^1$-Tyr were lyophilised. $L^1$-Tyr: ~1 mg. MS: $[C_{28}H_{51}NO_5]^{2+}$296.72 (experimental), 296.70 (calculated); $[C_{28}H_{50}N_9O_5]^+$ 592.40 (experimental), 592.39 (calculated). HPLC: 7.360 min (linear gradient, 0→60% B in A over 25 min). $^1$H NMR: δ 1.76, m, 2H, glutarate $CH_2$; 2.13, m, 2H, glutarate $CH_2$; 2.24, t, 2H glutarate $CH_2$; 2.92, m, 1H, tyrosine β $CH_2$; 3.20-3.35, tyrosine β $CH_2$ obscured by cage signals; 3.20, broad s, 6H, cage $CH_2$; 3.26, broad s, 6H, cage $CH_2$; 3.35, broad s, 6H, cage $CH_2$; 3.53, broad s, 6H cage $CH_2$; 4.61, m, 1H, tyrosine α CH; 6.88, d, 2H, tyrosine aromatic CH; 7.12, d, 2H, tyrosine aromatic CH.

Example 10 $L^2$-$(YaHxC)_2$

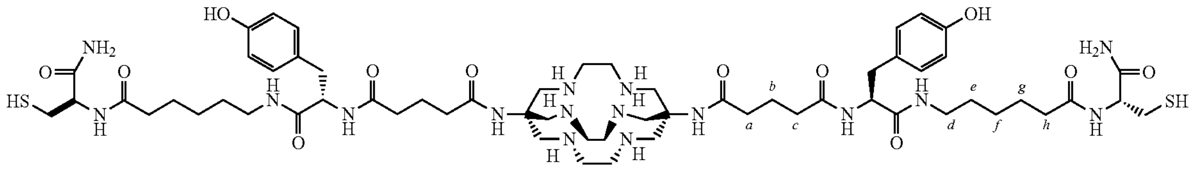

The synthesis of this molecule is as shown below:

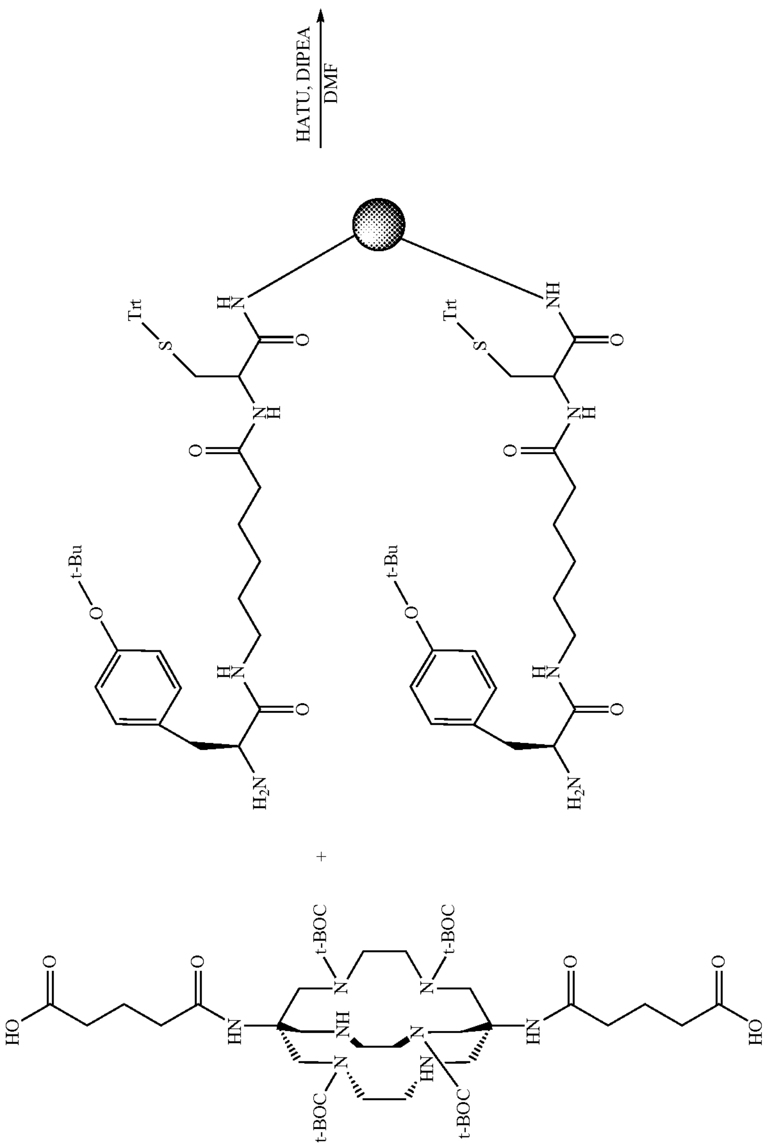
HATU, DIPEA
DMF

-continued
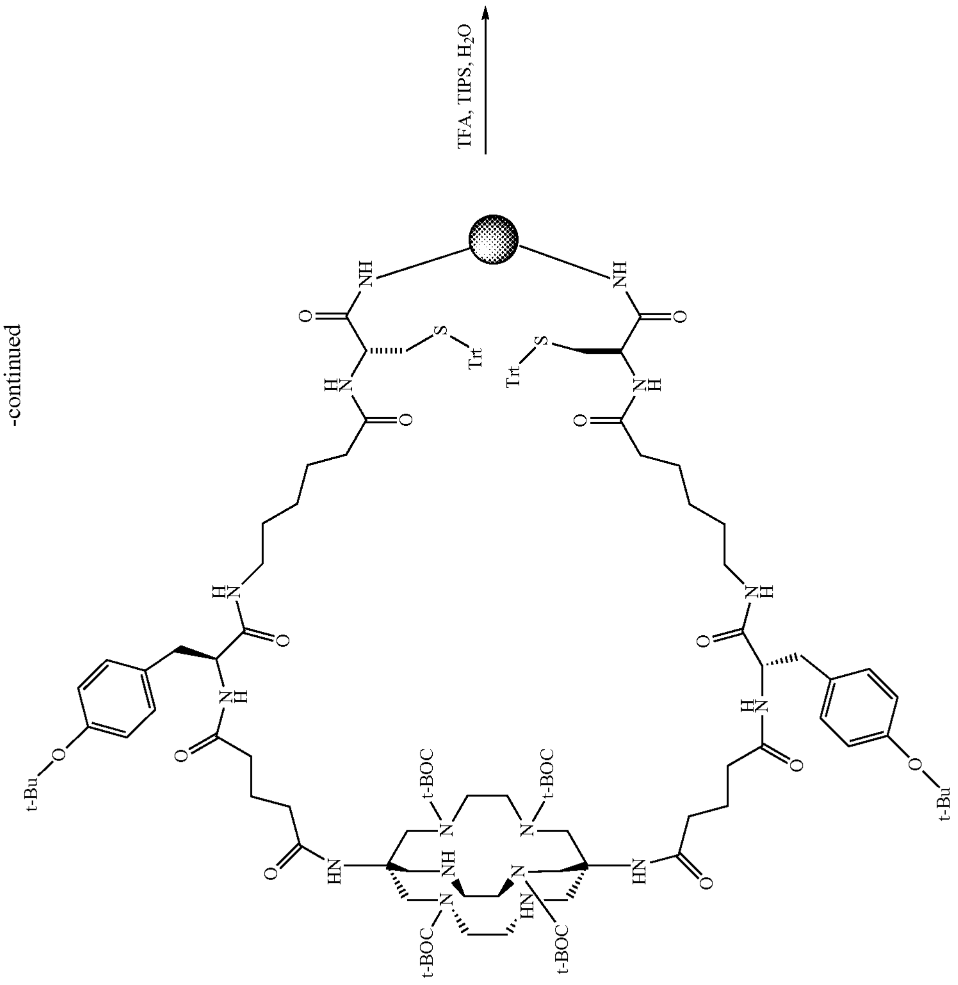

-continued
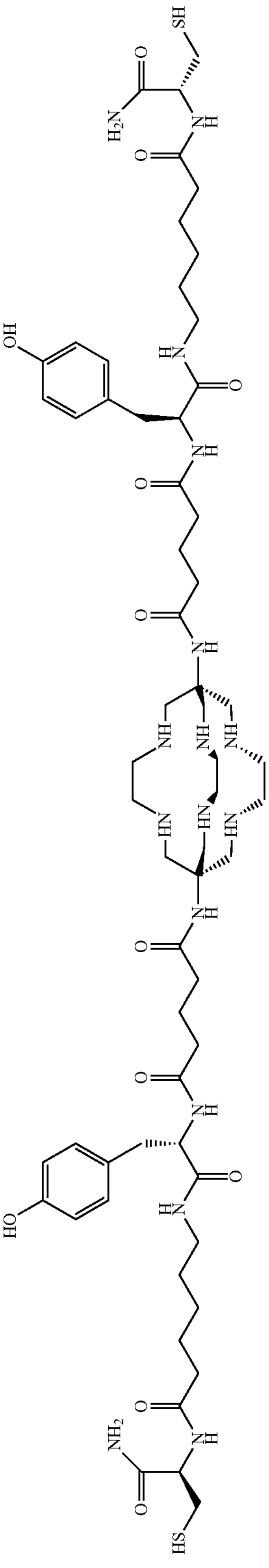
$L^2$-(YHxC)$_2$

Tyr(tBu)-aHx-Cys(Trt)-$NH_2$ was synthesised on Nova Peg Rink Amide resin with a loading of 0.67 mmol $g^{-1}$. HATU (8.9 mg, 0.02 mmol, 2 equivalents) in DMF (0.5 mL) and DIPEA (7 μL) was added to a solution of $L^2$-(t-Boc)$_4$ (10 mg, 0.01 mmol) in DMF (0.5 mL). This solution was added to Tyr(tBu)-aHx-Cys(Trt)-$NH_2$ on resin (0.05 g, ~0.22 mmol $g^{-1}$, ~0.01 mmol) and the mixture was left to react overnight. The reaction supernatant was then drained and the resin washed with DMF (3×5 mL) and DCM (3×5 mL). The resin was transferred to a falcon tube and trifluoroacetic acid (3 mL), deionised water (80 μL) and triisopropylsilane (80 u mL) were added. The falcon tube was placed on a shaker for 90 min. After this time, the solvent was evaporated under a stream of nitrogen gas, and the residue redissolved in A:B (50:50). This solution was filtered (MilliQ 0.45 μm syringe filter) and lyophilised.

The crude peptide material was purified by semi-preparative reverse phase HPLC (Eclipse XDB-C18 5 μm 9.5×250 mm column) using a linear 1% A→B/min gradient. $L^2$-(YHxC)$_2$ eluted at 27 min (determined by ESI-MS). Fractions containing $L^2$-(YHxC)$_2$ were lyophilised. This sample was subjected to a second HPLC purification where it eluted at 44 min using a linear 0.5% A→B/min gradient. $L_2$-(YHxC)$_2$: ~1 mg; HPLC retention time: 10.52 min (linear gradient, 0→60% B in A over 25 min) MS: $[C_{60}H_{100}N_{16}O_{12}S]^{2+}$650.36 (calculated), 650.36 (experimental); $[C_{60}H_{99}N_{16}O_{12}S]^{+}$ 1299.71 (calculated), 1299.71 (experimental) $^1$H NMR: δ 1.16, m, 4H, $CH_2$(f); 1.38, m, 4H, $CH_2$(e); 1.59, m, 4H, $CH_2$(g); 1.79, m, 4H, $CH_2$(b); 2.13, m, 4H, $CH_2$(a); 2.29, t, 4H, $CH_2$(c); 2.34, t, 4H, $CH_2$(h); 2.29-3.08, m, 8H, β$CH_2$ Tyr and Cys; 3.05, m, 2H, CH(d); 3.17, m, 2H, CH(d); 3.17, s, 12H, cage $CH_2$; 3.38, s, 12H, cage $CH_2$; 4.44-4.55, m, 4H, αCH Tyr and Cys; 6.89, d, 4H, Tyr ar; 7.18, d, 4H, Tyr ar;

Example 11 $L^2$-(YaHxC)

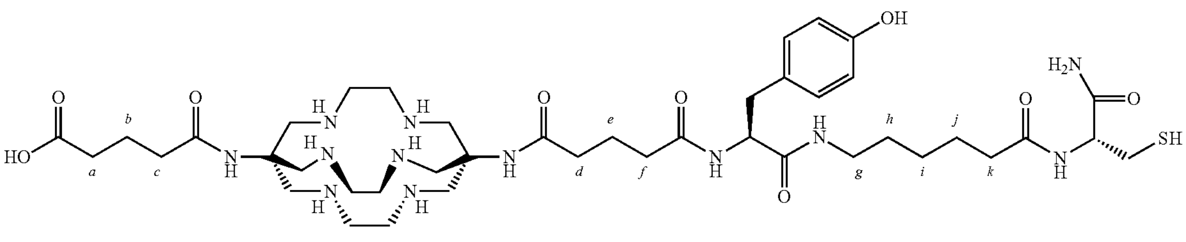

$L^2$-(YaHxC) was synthesised in the same way and on the same scale as $L^2$-(YaHxC)$_2$, except that instead of HATU, diisopropylcarbodiimide (7 μL) and hydroxybenzotriazole (3.5 mg) were used as coupling agents. A scheme is shown below.

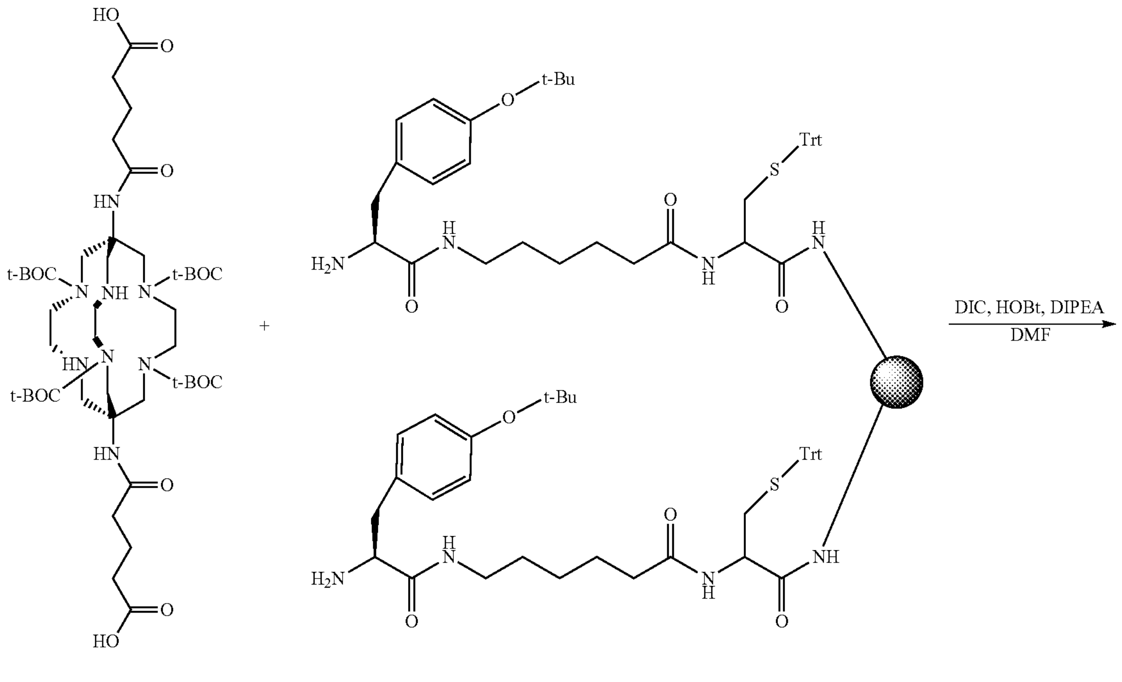

-continued

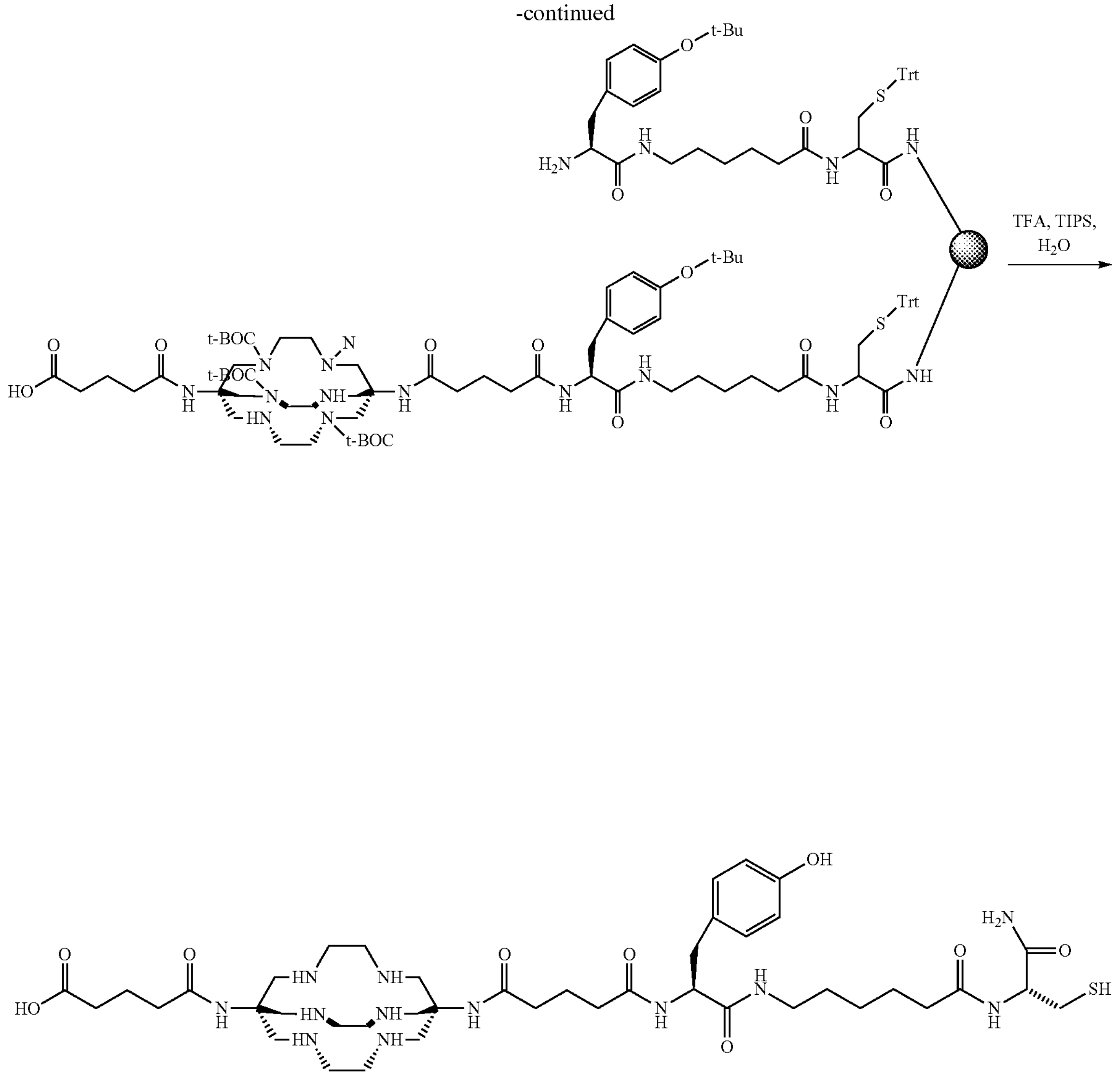

A mass spectrum of the crude peptide material indicated that both $L^2$-$(YaHxC)_2$ and $L^2$-(YaHxC) were present. The crude peptide material was purified by semi-preparative reverse phase HPLC (Eclipse XDB-C18 5 μm 9.5×250 mm column) using a linear 1% A→B/min gradient. $L^2$-(YHxC) eluted at 23.5 min and $L^2$-$(YaHxC)_2$ eluted at 28.5 min (determined by ESI-MS). Fractions containing $L^2$-(YHxC) were lyophilised. This sample was subjected to a second HPLC purification where it eluted at 35.8 min using a linear 0.5% A→B/min gradient. $L^2$-(YaHxC): ~0.2-0.6 mg; HPLC retention time: 8.73 min (linear gradient, 0→60% B in A over 25 min) MS: $[C_{42}H_{74}N_{12}O_9S]^{2+}$ 461.27 (experimental), 461.27 (calculated); $[C_{42}H_{73}N_{12}O_9S]^+$ 921.53 (calculated), 921.53 (experimental). $^1H$ NMR: δ 1.15, m, 2H, $CH_2$(i); 1.37, m, 2H, $CH_2$(h); 1.58, m, 2H, $CH_2$(j); 1.79, m, 2H, $CH_2$(e); 1.89, m, 2H, $CH_2$(b); 2.16, m, 2H, $CH_2$(d); 2.30, t, 2H, $CH_2$(f); 2.34, t, 2H, $CH_2$(k); 2.37, t, 4H, $CH_2$(a) and $CH_2$(c); 2.87-3.03, m, 4H, $\beta CH_2$ Tyr and Cys; 3.03, m, 1H, CH(g); 3.22, m, 1H, CH(g); 3.23, s, 12H, cage $CH_2$; 3.42, s, 6H, cage $CH_2$; 3.50, s, 6H, cage $CH_2$; 4.44-4.55, m, 2H, αCH Tyr and Cys; 6.89, d, 2H, Tyr ar; 7.18, d, 2H, Tyr ar;

Example 12 c(RGDfK(maleimidopropionate))

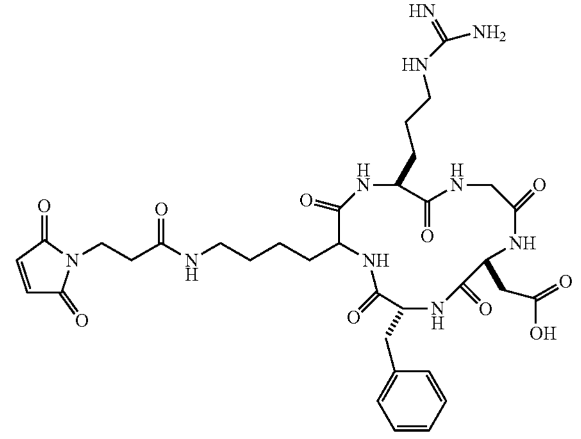 [SMILES: N=C(N)NCCC[C@@H]1NC(=O)C(CCCCNC(=O)CCN2C(=O)C=CC2=O)NC(=O)[C@@H](Cc2ccccc2)NC(=O)[C@@H](CC(=O)O)NC(=O)CNC1=O]

D(tBu)fK(ivDde)R(Pbf)G-OH (1 mmol) was synthesised on chlorotrityl resin (1 mmol $g^{-1}$, 1 g). The N-terminus was protected with trityl chloride to give Trt-D(tBu)fK(ivDde) R(Pbf)G-OH, followed by removal of the ivDde protecting group of the Lys side-chain using hydrazine (3×5 mL 5% hydrazine in DMF). Maleimidopropionic acid was then coupled to the Lys side-chain to give Trt-D(tBu)fK(maleimidopropionate)R(Pbf)G-OH. This species was concurrently deprotected at the N-terminus and cleaved from the resin using 2% TFA in DCM with radical scavengers to give D(tBu)fK(maleimidopropionate)R(Pbf)G-OH. The resulting solution was filtered and the solvent removed under reduced pressure, before HCTU (1 equivalent) and DIPEA (1 mL) in DCM (5 mL) were added to cyclise the peptide. The solution was stirred for 2 hours and after this time the solvent was removed under reduced pressure. The remaining protecting groups were then removed with TFA:$H_2O$:TIPS (95:2.5:2.5). The TFA was evaporated under a scream of nitrogen gas, and the crude material was redissolved in A:B (50:50), filtered and lyophilised. The crude peptide material was purified by semi-preparative reverse phase HPLC (Eclipse XDB-C18 5 μm 9.5×250 mm column) using a linear 1% A→B/min gradient. c(RGDfK(maleimidopropionate)) eluted at 28.5 min. c(RGDfK(maleimidopropionate)): 1-2 mg; HPLC retention time: 15.31 min (linear gradient, 0→60% B in A over 25 min) MS: $[C_{34}H_{46}N_{10}O_{10}]^+$ 755.35 (experimental), 755.35 (calculated).

Example 13 $L^2$-$(RGD)_2$

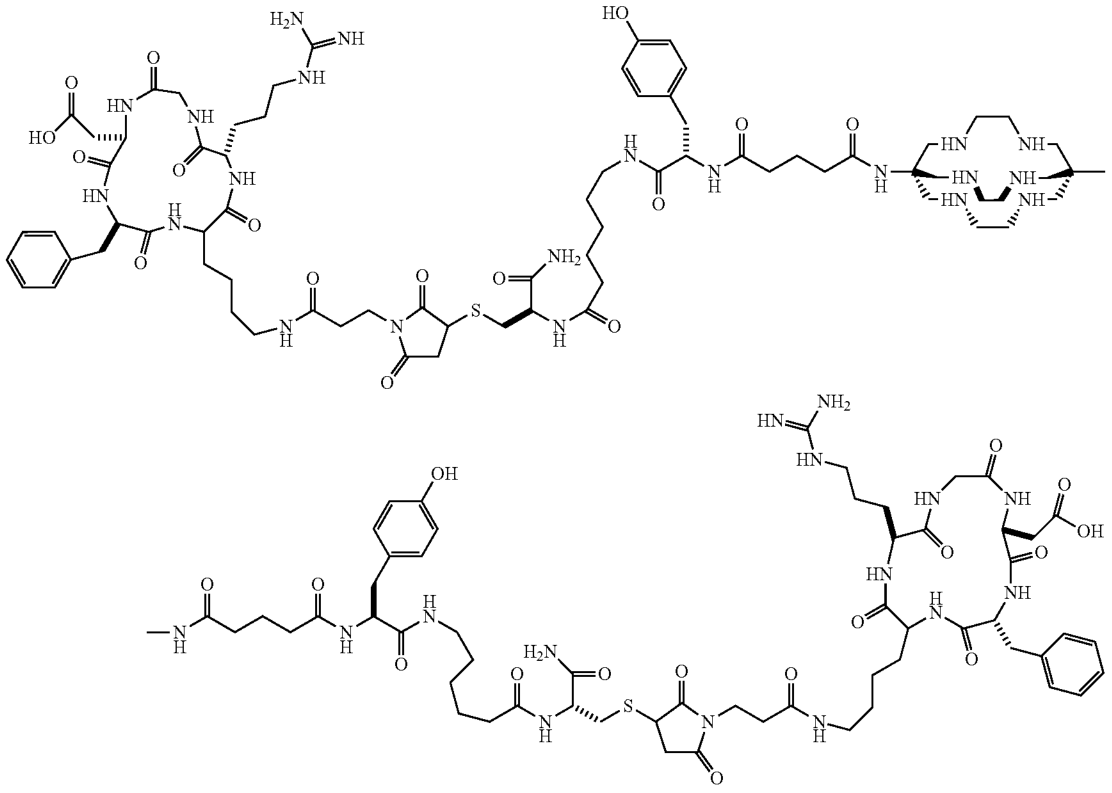

This molecule is synthesized as shown in the attached scheme:

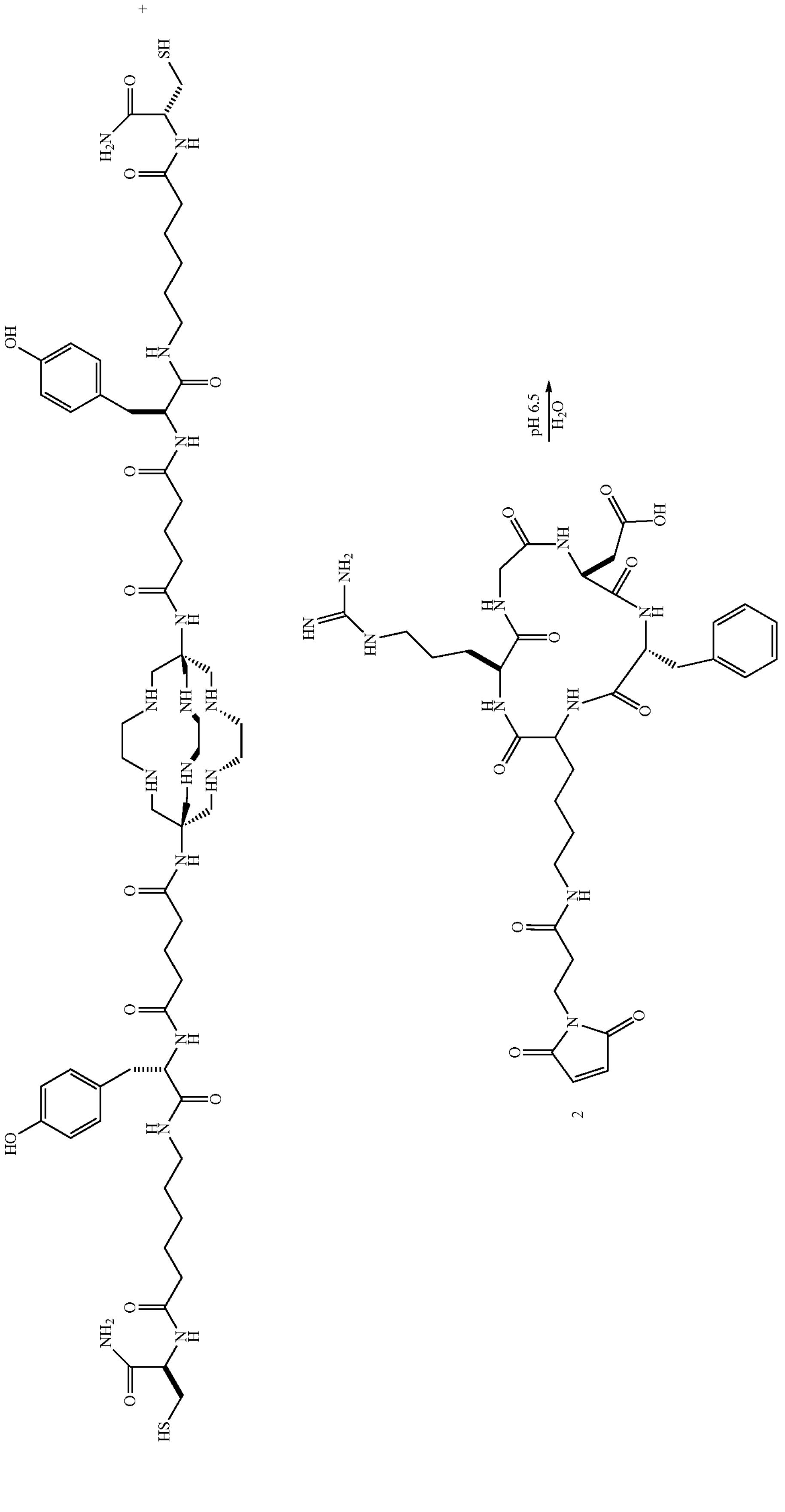
+
pH 6.5
$H_2O$
2

-continued
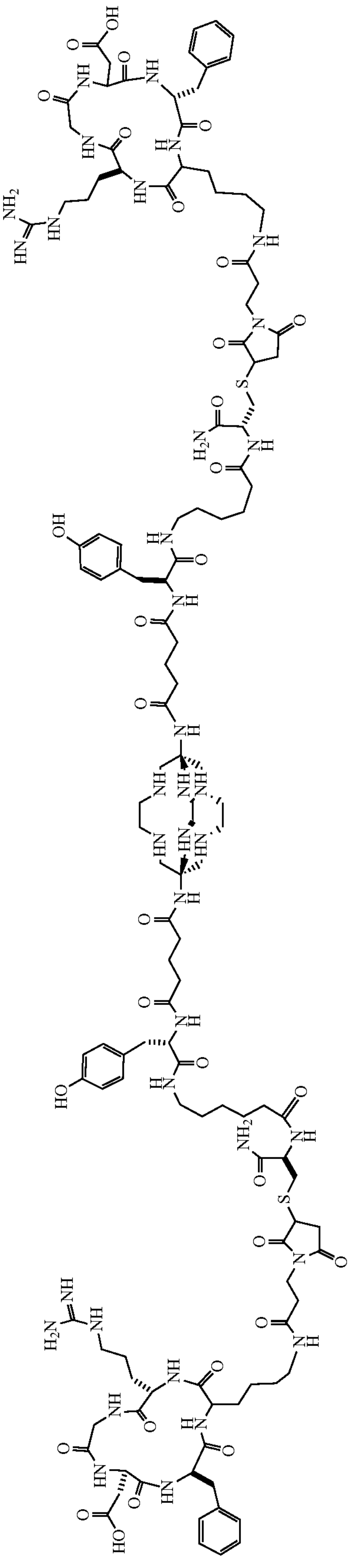

$L^2$-(YaHzC)$_2$ (~0.5 mg) and c(RGDfK(maleimidopropionate)) (~1 mg) were dissolved in ammonium acetate solution (25 mM, pH=6.5). After sitting at room temperature for ~30 min, the solution was purified by semi-preparative reverse phase HPLC (Eclipse XDB-C18 5 μm 9.5×250 mm column) using a linear 1% A→B/min gradient. c(RGDfK (maleimidopropionate)) eluted at 26 min and $L^2$-(RGD)$_2$ eluted at 29 min. $L^2$-(RGD)$_2$: $L^2$-(RGD)$_2$: ~1 mg; HPLC retention time: 16.54 min (linear gradient, 0→60% B in A over 25 min) MS: $[C_{128}H_{194}N_{36}O_{32}S_2]^{4+}$703.11 (experimental), 703.10 (calculated); $[C_{128}H_{193}N_{36}O_{32}S^2]^{3+}$937.14 (experimental), 937.13 (calculated).

Example 14 HPLC-MS of Sar-Peptides

HPLC-MS traces were acquired for Sar-peptides synthesised. HPLC-MS traces were also acquired for solutions containing Sar-peptide and $CuCl_2$, to determine whether Sar-peptide binds "free" $Cu^{2+}$ ion. We used a reverse phase C18 analytical HPLC column with a linear gradient (0→60% B in A over 25 min) to determine retention times and molecular masses of peptide species. (Here, A=milliQ water with 0.1% formic acid; B=acetonitrile with 0.1% formic acid.)

$L^1$-Tyr: $L^1$-Tyr (~10 μg) was dissolved in milliQ water (50 μL). This solution was further diluted (5 μL of peptide solution in 10 μL of milliQ water) to provide a solution of suitable concentration for HPLC-MS. A solution containing $L^1$-Tyr (5 μL of the original stock peptide solution) and $CuCl_2$ (10 μL of 1 mM $CuCl_2$ solution) in milliQ water (15 μL) was also made up. LCMS: $L^1$-Tyr, R.T.: 5.992; $[C_{28}H_{51}N9O_5]^{2+}$0 296.72 (experimental), 296.70 (calculated); $[C_{28}H_{50}N_9O_5]^+$ 592.40 (experimental), 592.39 (calculated); $[Cu(L^1\text{-Tyr})]^{x+}$, R.T.: 6.485; $[CuC_{28}H_{49}N_9O_5]^{2+}$ 327.17 (experimental), 327.16 (calculated), $[CuC_{28}H_{48}N9O_5]^+$653.31 (experimental), 653.31 (calculated).

$L^1$-Tyr$^3$-octreotate: $L^1$-Tyr$^3$-octreotate (~10 μg) was dissolved in milliQ water (50 μL). This solution was further diluted (5 μL of peptide solution in 20 μL of milliQ water) to provide a solution of suitable concentration for HPLC-ESI-MS. A solution containing $L^1$-Tyr$^3$-octreotate (5 μL of the original stock peptide solution) and $CuCl_2$ (5 μL of 1 mM $CuCl_2$ solution) in milliQ water (15 μL) was also made up. HPLC-ESI-MS: $L^1$-Tyr$^3$-octreotate, R.T.: 12.984 min; $[C_{68}H_{106}N_{18}O_{14}S_2]^{4+}$ 365.69 (experimental), 365.69 (calculated); $[C_{68}H_{105}N_{18}O_{14}S_2]^{3+}$ 487.25 (experimental), 487.25 (calculated); $[C_{68}H_{104}N_{18}O_{14}S_2]^{2+}$ 730.37 (calculated), 730.37 (experimental); $[Cu(L^1\text{-Tyr}^3\text{-octreotate})]^{x+}$, R.T.: 13.199 min; $[CuC_{68}H_{104}N_{18}O_{14}S_2]^{4+}$ 380.92 (experimental), 380.92 (calculated); $[CuC_{68}H_{103}N_{18}O_{14}S_2]^{3+}$ 507.56 (experimental), 507.55 (calculated); $[CuC_{68}H_{102}N_{18}O_{14}S_2]^{2+}$ 760.83 (calculated), 760.83 (experimental).

$(L^1)_2$-Tyr$^3$-octreotate: $(L^1)_2$-Tyr$^3$-octreotate (~10 μg) was dissolved in milliQ water (50 μL). This solution was further diluted (5 μL of peptide solution in 20 μL of milliQ water) to provide a solution of suitable concentration for HPLC-MS. A solution containing $(L^1)_2$-Tyr$^3$-octreotate (5 μL of the original stock peptide solution) and $CuCl_2$ (5 μL of 1 mM $CuCl_2$ solution) in milliQ water (15 μL) was also made up. LCMS: $(L^1)_2$-Tyr$^3$-octreotate, R.T.: 11.213; $[C_{87}H_{145}N_{26}O_{16}S_2]^{5+}$ 375.02 (experimental), 375.02 (calculated); $[C_{87}H_{14}N_{26}O_{16}S_2]^{4+}$468.52 (experimental), 468.52 (calculated); $[C_{87}H_{143}N_{26}O_{16}S_2]^{3+}$624.36 (experimental), 624.36 (calculated); $[C_{87}H_{142}N_{26}O_{16}S_2]^{2+}$ 936.03 (experimental), 936.03 (calculated); $[Cu_2(L^1)_2\text{-Tyr}^3\text{-octreotate}]^{x+}$, R.T.: 11.938; $[Cu_2C_{87}H_{141}N_{26}O_{16}S_2]^{5+}$ 399.58 (experimental), 399.58 (calculated); $[Cu_2C_{87}H_{140}N_{26}O_{16}S_2]^{4+}$ 499.23 (experimental), 499.23 (calculated); $[Cu_2C_{87}H_{139}N_{26}O_{16}S_2]^{3+}$ 665.30 (experimental), 665.29 (calculated).

$L^1$-Lys$_3$-bombesin: $L^1$-Lys$_3$-bombesin ((~1-5 μg) was dissolved in milliQ water (50 μL). The concentration of this solution was suitable for HPLC-ESI-MS. 1 mM $CuCl_2$ solution (2.5 L) was added to a portion of this solution (20 μL) to determine whether $L^1$-Lys$_3$-bombesin binds "free" $Cu^{2+}$ ion. HPLC-ESI-MS: $L^1$-Lys$_3$-bombesin, R.T.: 13.520 min; $[C_{90}H_{152}N^{30}O_{20}S]^{4+}$: 501.54 (experimental), 501.54 (calculated); $[C_{90}H_{151}N_{30}O_{20}S]^{3+}$: 668.39 (experimental), 668.38 (calculated); $[C_{90}H_{150}N_{30}O_{20}S_2]^{2+}$: 1002.07 (experimental), 1002.07 (calculated); $[Cu(L^1\text{-Lys}_3\text{-bombesin})]^{x+}$, R.T.: 13.769 min; $[CuC_{90}H_{150}N_{30}O_{20}S]^{4+}$: 517.02 (experimental), 517.02 (calculated); $[CuC_{90}H_{149}N_{30}O_{20}S]^{3+}$: 689.03 (experimental), 689.02 (calculated); $[CuC_{90}H_{148}N_{30}O_{20}S]^{2+}$: 1033.03 (experimental), 1033.03 (calculated).

Example 15 Radiolabelling with $^{64}Cu$ $^{64}CuCl_2$ (1.88 GBq/mL, 0.1 M HCl pH 1) was purchased from ANSTO radiopharmaceuticals and industrials (ARI), Lucas Heights, NSW, Australia. The radionuclidic purity at calibration $\{(^{64}Cu)/(^{67}Cu)\}$ was 100% and the radiochemical purity as $Cu^{2+}$ was 100%. The chemical purity of copper, zinc and iron were 1.1 μg/mL, 0.9 μg/mL and 10 μg/mL respectively.

HPLC with a radioactivity sodium iodide scintillation detector was used to monitor $L^1$-peptide ligation to $^{64}Cu^{2+}$. We employed a reverse phase C18 analytical HPLC column with a linear gradient (0→60% B in A over 15 min) to determine retention times of $[^{64}CuL^1\text{-peptides}]^{2+}$. These retention times were compared with retention times of the "cold" $[CuL^1\text{-peptides}]^{2+}$ under the same HPLC conditions with UV spectroscopic detection at 275 nm.

$[^{64}Cu(L^1)]^{2+}$: Trace 1: $^{64}CuCl_2$ (38 MBq, 20 μL, 0.1 M HCl) was added to an aqueous solution (580 μL) containing $L^1$ (0.015 mg/mL) and sodium acetate (0.015 M). The pH was ~4.5 (measured with pH strips). The solution was left at ambient temperature for 10 min before an aliquot (100 μL) was injected onto a reverse phase C18 analytical HPLC column with a linear gradient (0→60% B in A over 15 min). Retention time: 2.33 min, ~82% radiochemical yield. Retention time: 8.36, ~18% radiochemical yield. Trace 2: Sodium acetate solution (100 μL, 0.1 M) was added to the remainder of the above solution. The pH was ≥5.5. An aliquot of this solution (100 μL) was injected onto a reverse phase C18 analytical HPLC column with a linear gradient (0→60% B in A over 15 min). Retention time: 8.334 min, >95% radiochemical yield. Trace 3: $^{64}CuCl_2$ (38 MBq, 20 μL, 0.1 M HCl) was added to the remainder of the above solution to increase the signal to noise ratio, as well as determine the time required to complex 100% of $^{64}Cu^{2+}$ present in solution. A further aliquot of sodium acetate (100 μL, 0.1 M) solution was added. The solution was left to stand at ambient temperature for 5 min before an aliquot was injected onto a reverse phase C18 analytical HPLC column with a linear gradient (0→60% B in A over 15 min). Retention time: 8.334 min, >95% radiochemical yield. An aqueous sample of "cold" $[Cu(L^1)](NO_3)_3$ (~1 mg/ml) was injected onto the HPLC column (injection volume ~30 μL) and was eluted using the same linear gradient (0→60% B in A over 15 min). Retention time: 8.573 min.

[$^{64}$Cu(L$^1$-Tyr)]$^{2+}$: $^{64}CuCl_2$ (19 MBq, 10 μL, 0.1 M HCl) was added to an aqueous solution (490 μL) containing L$^1$-Tyr (0.02 mg/mL) and sodium acetate (0.02 M). The solution was left at ambient temperature for 10 min before an aliquot (100 μL) was injected onto a reverse phase C18 analytical HPLC column with a linear gradient (0→60% B in A over 15 min). Retention time: 10.231 min, >95% radiochemical yield. An 25 aqueous sample of "cold" [Cu (L$^1$-Tyr)]$^{2+}$: (~1 mg/mL) was injected onto the HPLC column (injection volume ~30 μL) and was eluted using the same linear gradient (0→60% B in A over 15 min). Retention time: 10.403 min

[$^{64}$CuL$^1$-Tyr$^3$-octreotate]$^{2+}$: An aliquot of 0.1 M HCl solution containing 64CuCl$^2$ (38 MBq, 20 μL, 0.1 M HCl) was added to an aqueous solution (490 μL) containing L$^1$-Tyr$^3$-octreotate (0.02 mg/mL) and sodium acetate (0.02 M). The pH was ≥5.5. The solution was left at ambient temperature for 20 min before an aliquot (100 uL) was injected onto a reverse phase C18 analytical HPLC column with a linear gradient (0→60% B in A over 15 min). Retention time: 12.730 min, >95% radiochemical yield. An aqueous sample of "cold" [CuL$^1$-Tyr$^3$-octreotate]$^{2+}$ (~1 mg/mL) was injected onto the HPLC column (injection volume ~30 μL) and was eluted using the same linear gradient (0→60% B in A over 15 min). Retention time: 12.937 min.

Human male AB serum (200 μL) was added to a solution of [$^{64}$CuL$^1$-Tyr$^3$-octreotate]$^{2+}$ (200 μL). This solution was incubated in a water bath at 37° C. At time points of 1 hr, 4 hr and 20 hr an aliquot of this serum solution (100 μL) was removed for radio-HPLC analysis: acetonitrile (200 μL) was added to the serum aliquot to precipitate serum proteins. This mixture was filtered and the acetonitrile evaporated under a stream of argon gas. The final volume was <100 μL. The solution was frozen at −70° C. until injection onto the HPLC column. 1 hr: Retention time 12.716 min, >95% radiochemical yield; 4 hr: Retention time 12.725 min, >95% radiochemical yield; 20 hr: Retention time 12.800 min, >95% radiochemical yield.

[$^{64}$CuL$^1$-Lys$_3$-bombesin]$^{2+}$: An aliquot of 0.1 M HCl solution containing $^{64}CuCl_2$ (38 MBq, 20 μL, 0.1 M HCl) was added to an aqueous solution (290 μL) containing L$^1$-Lys$_3$-bombesin (~0.03 mg/mL) and sodium acetate (0.03 M). The solution was left at ambient temperature for 10 min before an aliquot (100 μL) was injected onto a reverse phase C18 analytical HPLC column with a linear gradient (0→60% B in A over 15 min). Retention time: 12.642; >95% radiochemical yield. An aqueous sample of "cold" [CuL$^1$-Lys$_3$-bombesin]$^{2+}$ (~0.5 mg/mL) was injected onto the HPLC column (injection volume ~60 μL) and was eluted using the same linear gradient (0→60% B in A over 15 min). Retention time: 13.073 min.

A single time point serum stability study for [$^{64}$CuL$^1$-Lys$_3$-bombesin]$^{2+}$ was conducted in the same way as studies for [$^{64}$CuL$^1$-Tyr$^3$-octreotate]$^{2+}$. An aliquot of [$^{64}$CuL$^1$-Lys$_3$-bombesin]$^{2+}$ (200 μL) was added to human male AB serum and incubated at 37° C. After 2 hr, the sample was subjected to the same treatment as described above and injected onto the HPLC column. 2 hr: Retention time 12.828 min, >95% radiochemical yield.

Finally, it will be appreciated that various modifications and variations of the methods and compositions of the invention described herein will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are apparent to those skilled in the art are intended to be within the scope of the present invention.

The invention claimed is:

1. A method of producing a compound of formula (I),

Formula (I)

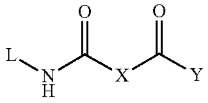

wherein:

L is a nitrogen containing macrocyclic metal ligand;

X is a linking moiety;

Y is selected from the group consisting of OR, $SR^1$ and $N(R^2)_2$;

R is independently selected from the group consisting of H, an oxygen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

$R^1$ is independently selected from the group consisting of H, a sulfur protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl; and each $R^2$ is independently selected from the group consisting of H, a nitrogen protecting group, optionally substituted $C_1$-$C_{12}$alkyl, optionally substituted $C_2$-$C_{12}$alkenyl, optionally substituted $C_2$-$C_{12}$alkynyl and optionally substituted $C_2$-$C_{12}$ heteroalkyl;

or a pharmaceutically acceptable salt or complex thereof, the method comprising:

reacting an amino substituted metal chelating ligand or a metal complex thereof of the formula:

$L\text{-}NH_2$ wherein L is a nitrogen containing macrocyclic metal ligand; with an activated dicarbonyl compound of the formula (III)

Formula (III)

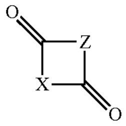

wherein Z is O, S or $NR^2$; and (b) isolating the compound of formula (I) or a metal complex thereof;

wherein L is

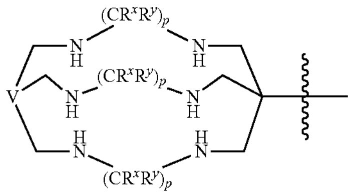

V is selected from the group consisting of N and $CR^4$;

each $R^x$ and $R^y$ are independently selected from the group consisting of H, $CH_3$, $CO_2H$, $NO_2$, $CH_2OH$, $H_2PO_4$, $HSO_3$, CN, $CONH_2$ and CHO;

each p is independently an integer selected from the group consisting of 2, 3, and 4, $R^4$ is selected from the group consisting of H, OH, halogen, $NO_2$, $NH_2$, optionally substituted $C_1$-$C_{12}$alkyl, optionally substituted $C_6$-$C_{18}$aryl, cyano, $CO_2R^5$, $NHR^5$, $N(R^5)_2$ and a group of the formula:

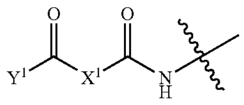

wherein $X^1$ is a linking moiety;

$Y^1$ is selected from the group consisting of $OR^6$, $SR^7$, $N(R^8)_2$ and a molecular recognition moiety;

wherein $R^5$ is H or $C_1$-$C_{12}$alkyl, wherein $R^6$ is selected from the group consisting of H, halogen, an oxygen protecting group, optionally substituted $C_1$-$C_{12}$alkyl, optionally substituted $C_2$-$C_{12}$-alkenyl, optionally substituted $C_2$-$C_{12}$alkynyl and optionally substituted $C_2$-$C_{12}$ heteroalkyl;

wherein $R^7$ is selected from the group consisting of H, halogen, a sulfur protecting group, optionally substituted $C_1$-$C_{12}$alkyl, optionally substituted $C_2$-$C_{12}$-alkenyl, optionally substituted $C_2$-$C_{12}$alkynyl and optionally substituted $C_2$-$C_{12}$ heteroalkyl;

wherein $R^8$ is independently selected from the group consisting of H, halogen, a nitrogen protecting group, optionally substituted $C_1$-$C_{12}$alkyl, optionally substituted $C_2$-$C_{12}$-alkenyl, optionally substituted $C_2$-$C_{12}$alkynyl and optionally substituted $C_2$-$C_{12}$ heteroalkyl.

2. The method according to claim 1, wherein the leaving group is selected from the group consisting of Cl, Br, $CH_3SO_3$, $CH_3C_6H_4SO_3$, and a group of the formula:

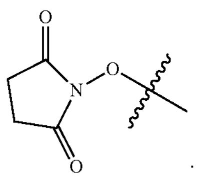 [SMILES: *ON1C(=O)CCC1=O]

3. The method according to claim 1 wherein the amino substituted metal chelating ligand and the activated dicarbonyl compound are reacted in the presence of a base.

4. The method according to claim 3, wherein the base is diisopropylethylamine.

5. The method according to claim 1 wherein L comprises a metal.

6. A method of radioimaging a subject, the method comprising administering an effective amount of the compound according to claim 1 to the subject, wherein the nitrogen containing macrocyclic metal ligand is coordinated with a metal ion.

* * * * *

SEQUENCE LISTING

```
Sequence total quantity: 2
SEQ ID NO: 1            moltype = AA  length = 8
FEATURE                 Location/Qualifiers
REGION                  1..8
                        note = Linear octreotate peptide
SITE                    1
                        note = MISC_FEATURE - dPhe
SITE                    4
                        note = MISC_FEATURE - dTrp
source                  1..8
                        mol_type = protein
                        organism = synthetic construct
SEQUENCE: 1
FCYWKTCT                                                     8

SEQ ID NO: 2            moltype = AA  length = 14
FEATURE                 Location/Qualifiers
REGION                  1..14
                        note = Bombesin peptide
SITE                    1
                        note = MISC_FEATURE - Pyr
source                  1..14
                        mol_type = protein
                        organism = synthetic construct
SEQUENCE: 2
XQKLGNQWAV GHLM                                              14
```